United States Patent
Datta et al.

(10) Patent No.: US 8,658,376 B2
(45) Date of Patent: *Feb. 25, 2014

(54) DEK AS A URINE BASED BIOMARKER FOR BLADDER CANCER

(75) Inventors: Antara Datta, Hillsborough, NJ (US); Jason Trama, Burlington, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/317,532

(22) Filed: Oct. 20, 2011

(65) Prior Publication Data

US 2012/0190046 A1   Jul. 26, 2012

Related U.S. Application Data

(60) Provisional application No. 61/455,406, filed on Oct. 20, 2010, provisional application No. 61/455,405, filed on Oct. 20, 2010.

(51) Int. Cl.
*G01N 33/574* (2006.01)
*C12Q 1/00* (2006.01)

(52) U.S. Cl.
USPC ................................. 435/7.1; 435/7.23; 435/4

(58) Field of Classification Search
None
See application file for complete search history.

(56) References Cited

U.S. PATENT DOCUMENTS

2009/0004197 A1* 1/2009 Markovitz et al. ......... 424/141.1

OTHER PUBLICATIONS

Thongboonkerd et al, Kidney International 62:1461-1469, 2002.*
Hu et al., Effects of Gag Mutation, Feb. 2006, Journal of Virology, pp. 1242-1249, vol. 80, No. 3.
Alvarez A., and V. B. Lokeshwar. Bladder cancer biomarkers: current developments and future implementation. Curr Opin Urol, 2007. 17:341-6.
Stenzl A., J. Hennenlotter, and D. Schilling. Can we still afford bladder cancer? 2008. Curr Opin Urol 18:488-92.
Kaufman D.S., W.U. Shipley, and A.S. Feldman. Bladder cancer. Jun. 10, 2009. Lancet, 374(9685): 239-49.
Van Tilborg V A. A., et al. Bladder cancer biomarkers and their role in surveillance and screening. Oct. 21, 2008, Int J Urol 16:23-30.
Carro M. S., et al. DEK Expression is controlled by E2F and deregulated in diverse tumor types. Jun. 1, 2006. Cell Cycle 5:1202-7.
Respaldiza, W.N., Jr. et al. Autoantibodies to DEK oncoprotein in a patient with systemic lupus erythematosus. Nov. 10, 1999, Clin. Exp. Immunol 119: 530-532.
Sanchez-Carbayo, M., N. D. Socci, et al. Gene discovery in bladder cancer progression using cDNA microarrays. Aug. 2003. Am J Pathol 163:505-16.
Wise-Draper, T. M., et. al., Apoptosis inhibition by the human DEK oncoprotein involves interference with p53 functions. Oct. 2006. Mol Cell Biol 26:7506-19.
Wise-Draper, T. M., et. al. The human DEK proto-oncogene is a senescence inhibitor and an upregulated target of high-risk human papillomavirus E7. Nov. 2005. J Virol 79:14309-17.
Wise-Draper, T. M., et. al. Mar. 1, 2009. Overexpression of the cellular DEK protein promotes epithelial transformation in vitro and in vivo. Cancer Res 69:1792-9.
Wise-Draper, T. M., et. al. Jan. 2009. DEK proto-oncogene expression interferes with the normal epithelial differentiation program. Am J Pathol 174:71-81.
Wu Q., M. J. Hoffmann, F. H. Hartmann, and W. A. Schulz. May 5, 2005. Amplification and overexpression of the ID4 gene at 6p22.3 in bladder cancer. Mol Cancer 4:16.
Soengas, M.S., and E. Riveiro-Falkenbach. Control of tumorigenesis and chemoresistance by DEK oncogene. Jun. 2010. Clin. Cancer. Res. 16:(11) 2932-2938.
Cancer Facts and Figures 2010, American Cancer Society, Altanta.
O'Sullivan, et al., Methods for the Preparation of Enzyme-antibody Conjugates for Use in Enzyme Immunoassay, 1981, Methods of Enzymology, pp. 147-166, vol. 73, Academic Press, NY, NY.
Datta, et al, Oncoprotein DEK as a tissue and urinary biomarker for bladder cancer, 2011, BMC Cancer, vol. 11, 234.

* cited by examiner

*Primary Examiner* — Lei Yao
(74) *Attorney, Agent, or Firm* — Siu K. Lo

(57) ABSTRACT

The present invention is directed to a method of detecting DEK protein in a urine sample. Methods and compositions are provided herein for detecting and diagnosing bladder cancer by chemical-induced precipitation of urine proteins, followed by filtration-induced concentration and Western blot analysis to specifically detect DEK protein. The present method permits specific detection of DEK protein in urine as a biomarker for bladder cancer in humans.

10 Claims, 18 Drawing Sheets

SEQUENCE LISTING

```
<160> NUMBER OF SEQ ID NOS: 4

<210> SEQ ID NO 1
<211> LENGTH: 2879
<212> TYPE: DNA
<213> ORGANISM: Homo sapiens

<400> SEQUENCE: 1
cattcccgct ctccttcccg aaccgccatt ttgaaaatct tgttgattct ggggagccga      60
gcgcgcggcg cgagcgtcac gccagacagc ggcccgcgcg ccttctcctc ggcgtcggcc     120
gccgccgcct cccagaacct cctcgtgccc tcgcgtgcca ggcccgcggc ggccgaaatc     180
cgcggttcac agcatgtccg cctcggcccc tgctgcggag ggggagggaa ccccaccca     240 gcccgcgtcc gagaaagaac ccgaaatgcc cggtcccaga gaggagagcg aggaggaaga     300
ggacgaggac gacgaggagg aggaggagga ggaaaaagaa aagagtctca tcgtggaagg     360
caagagggaa aagaaaaaag tagagaggtt gacaatgcaa gtctcttcct tacagagaga     420
gccatttaca attgcacaag gaaaggggca gaaactttgt gaaattgaga ggatacattt     480
ttttctaagt aagaagaaaa ccgatgaact tagaaatcta cacaaactgc tttacaacag     540
gccaggcact gtgtcctcat taaagaagaa tgtgggtcag ttcagtggct ttccatttga     600
aaaaggaagt gtccaatata aaagaagga agaaatgttg aaaaaattta gaaatgccat     660
gttaaagagc atctgtgagg ttcttgattt ggagagatca ggtgtaaata gtgaactagt     720
gaagaggatc ttgaatttct taatgcatcc aaagccttct ggcaaaccat tgccgaaatc     780
taaaaaaact tgtagcaaag gcagtaaaaa ggaacggaac agttctggaa tggcaaggaa     840
ggctaagcga accaaatgtc ctgaaattct gtcagatgaa tctagtagtg atgaagatga     900 aagaaaaac aaggaagagt cttcagatga tgaagataaa gaaagtgaag aggagccacc     960
aaaaaagaca gccaaaagag aaaaacctaa acagaaagct acttctaaaa gtaaaaaatc    1020
tgtgaaaagt gccaatgtta agaaagcaga tagcagcacc accaagaaga atcaaaacag    1080
ttccaaaaaa gaaagtgagt ctgaggatag ttcagatgat gaacctttaa ttaaaagtt    1140 gaagaaaccc cctacagatg aagagttaaa ggaaacaata aagaaattac tggccagtgc    1200
taacttggaa gaagtcacaa tgaaacagat ttgcaaaaag gtctatgaaa attatcctac    1260
ttatgattta actgaaagaa aagatttcat aaaaacaact gtaaaagagc taatttcttg    1320
agatagagga cagagaagat gactcgttcc catagatttg aagatctgat ttataccatt    1380
ataccagcaa agagaatgta tttccttttc taaatccttg ttaagcaacg ttagtagaac    1440
ttactgctga ccttttatc ttgagtgtta tgtgaatttg agtttgctgt tttaaattgc    1500
```

```
atttctatgc catttttagt ttaaaatctt gcatggcatt aattgttcct tgcttttata      1560
gttgtatttt gtacattttg gatttcttta tataaggtca tagattcttg agctgttgtg      1620
gttttagtg cacttaatat tagcttgctt aaggcatact tttaatcaag tagaacaaaa       1680
actattatca ccaggattta tacatacaga gattgtagta tttagtatat gaaatatttt      1740
gaatacacat ctctgtcagt gtgaaaattc agcggcagtg tgtccatcat attaaaaata     1800
tacaagctac agttgtccag atcactgaat tggaactttt ctcctgcatg tgtatatatg     1860
tcaaattgtc agcatgacaa aagtgacaga tgttatttt gtatttttaa aaaacaattg      1920
gttgtatata aagtttttt atttctttg tgcagatcac ttttaaact cacataggta        1980
ggtatcttta tagttgtaga ctatggaatg tcagtgttca gccaaacagt atgatggaac     2040
agtgaaagtc aattcagtga tgcaacacct gaaggaacag ttaccctgct ttgcctcgaa     2100
agtgtcatca atttgtaatt ttagtattaa ctctgtaaaa gtgtctgtag gtacgttta     2160
tattatataa ggacagacca aaaatcaacc tatcaaagct tcaaaaactt tgggaaaggg    2220
tgggattaag tacaagcaca tttggcttac agtaaatgaa ctgatttta ttaactgctt    2280
ttgcccatat aaaatgctga tatttactgg aaacctagcc agcttcacga ttatgactaa   2340
agtaccagat tataatgcca gaatataatg tgcaggcaat cgtggatgtc tctgacaaag  2400
tgtgtctcaa aataatata cttttacatt aaagaaattt aatgtttctc tggagttggg     2460
gctcttggct ttcagagttt ggttaatcag tgttgattct agatgatcaa cataatggac    2520
cactcctgaa tgagacttaa ttttgtcttt caaatttact gtcttaaatc agtttattaa   2580
atctgaattt taaaacatgc tgtttatgac acaatgacac atttgttgca ccaattaagt    2640
gttgaaaaat atctttgcat catagaacag aaatatataa aaatatatgt tgaatgttaa    2700
caggtatttt cacaggtttg tttcttgata gttactcaga cactagggaa aggtaaatac    2760
aagtgaacaa aataagcaac taaatgagac ctaataattg gccttcgatt ttaaatattt    2820
gttcttataa accttgtcaa taaaaataaa tctaaatcac tggtgtttta aaaaaaaaa   2879
```

<210> SEQ ID NO 2
<211> LENGTH: 2785
<212> TYPE: DNA
<213> ORGANISM: Homo sapiens

<400> SEQUENCE: 2

```
cattcccgct ctccttcccg aaccgccatt ttgaaaatct tgttgattct ggggagccga     60
gcgcgcggcg cgagcgtcac gccagacagc ggcccgcgcg ccttctcctc ggcgtcggcc    120
gccgccgcct cccagaacct cctcgtgccc tcgcgtgcca ggcccgcggc ggccgaaatc   180
cgcggttcac agcatgtccg cctcggcccc tgctgcggag ggggagggaa cccccacccca  240
gcccgcgtcc gagaaagaac ccgaaatgcc cggtcccaga gaggagagcg aggaggaaga   300
ggacgaggac gacgaggagg aggaggagga ggaaaaagga aagggcagaa actttgtga    360
aattgagagg atacattttt ttctaagtaa gaagaaaacc gatgaactta gaaatctaca   420
caaactgctt tacaacaggc caggcactgt gtcctcatta agaagaatg tgggtcagtt    480
cagtggcttt ccatttgaaa aaggaagtgt ccaatataaa agaaggaag aatgttgaa     540
aaaatttaga aatgccatgt taagagcat ctgtgaggtt cttgatttgg agagatcagg    600
tgtaaatagt gaactagtga agaggatctt gaatttctta atgcatccaa agccttctgg   660
caaaccattg ccgaaatcta aaaaaacttg tagcaaaggc agtaaaaagg aacgaacag    720
ttctggaatg gcaaggaagg ctaagcgaac caaatgtcct gaaattctgt cagatgaatc   780
```

```
tagtagtgat gaagatgaaa agaaaaacaa ggaagagtct tcagatgatg aagataaaga    840
aagtgaagag gagccaccaa aaaagacagc caaaagagaa aaacctaaac agaaagctac    900
ttctaaaagt aaaaaatctg tgaaaagtgc caatgttaag aaagcagata gcagcaccac    960
caagaagaat caaacagtt ccaaaaaga agtgagtct gaggatagtt cagatgatga      1020
acctttaatt aaaagttga agaaacccc tacagatgaa gagttaaagg aaacaataaa     1080
gaaattactg gccagtgcta acttggaaga agtcacaatg aaacagattt gcaaaaaggt   1140
ctatgaaaat tatcctactt atgatttaac tgaaagaaaa gatttcataa aaacaactgt   1200
aaaagagcta atttcttgag atagaggaca gagaagatga ctcgttccca tagatttgaa   1260
gatctgattt ataccattat accagcaaag agaatgtatt tccttttcta aatccttgtt   1320
aagcaacgtt agtagaactt actgctgacc tttttatctt gagtgttatg tgaatttgag   1380
tttgctgttt taaattgcat ttctatgcca tttttagttt aaaatcttgc atggcattaa   1440
ttgttccttg ctttttatagt tgtatttttgt acattttgga tttctttata taaggtcata 1500
gattcttgag ctgttgtggt ttttagtgca cttaatatta gcttgcttaa ggcatacttt   1560
taatcaagta gaacaaaaac tattatcacc aggatttata catacagaga ttgtagtatt   1620
tagtatatga aatatttga atacacatct ctgtcagtgt gaaaattcag cggcagtgtg    1680
tccatcatat taaaaatata caagctacag ttgtccagat cactgaattg gaactttttct 1740
cctgcatgtg tatatatgtc aaattgtcag catgacaaaa gtgacagatg ttattttgt    1800
atttttaaaa aacaattggt tgtatataaa gttttttat ttcttttgtg cagatcactt    1860
tttaaactca cataggtagg tatctttata gttgtagact atggaatgtc agtgttcagc   1920
caaacagtat gatggaacag tgaaagtcaa ttcagtgatg gcaacactga aggaacagtt   1980
accctgcttt gcctcgaaag tgtcatcaat ttgtaatttt agtattaact ctgtaaaagt   2040
gtctgtaggt acgttttata ttatataagg acagaccaaa aatcaaccta tcaaagcttc   2100
aaaaactttg ggaagggtg ggattaagta caagcacatt tggcttacag taaatgaact    2160
gatttttatt aactgctttt gcccatataa aatgctgata tttactggaa acctagccag   2220
cttcacgatt atgactaaag taccagatta taatgccaga atataatgtg caggcaatcg   2280
tggatgtctc tgacaaagtg tgtctcaaaa ataatatact tttacattaa agaaatttaa   2340
tgtttctctg gagttggggc tcttggcttt cagagtttgg ttaatcagtg ttgattctag   2400
atgatcaaca taatggacca ctcctgaatg agacttaatt ttgtctttca aatttactgt   2460
cttaaatcag tttattaaat ctgaatttta aaacatgctg tttatgacac aatgacacat   2520
ttgttgcacc aattaagtgt tgaaaatat ctttgcatca tagaacagaa atatataaaa    2580
atatatgttg aatgttaaca ggtatttttca caggtttgtt tcttgatagt tactcagaca  2640
ctagggaaag gtaaatacaa gtgaacaaaa taagcaacta aatgagacct aataattggc   2700
cttcgatttt aaatatttgt tcttataaac cttgtcaata aaaataaatc taaatcactg   2760
gtgttttaaa aaaaaaaaaa aaaaa                                         2785
```

<210> SEQ ID NO 3
<211> LENGTH: 375
<212> TYPE: PRT
<213> ORGANISM: Homo sapiens

<400> SEQUENCE: 3

Met Ser Ala Ser Ala Pro Ala Ala Glu Gly Glu Gly Thr Pro Thr Gln
1               5                   10                  15

Pro Ala Ser Glu Lys Glu Pro Glu Met Pro Gly Pro Arg Glu Glu Ser

```
                20                  25                  30
Glu Glu Glu Glu Asp Glu Asp Glu Glu Glu Glu Glu Glu Lys
             35                  40                  45

Glu Lys Ser Leu Ile Val Glu Gly Lys Arg Glu Lys Lys Val Glu
         50                  55                  60

Arg Leu Thr Met Gln Val Ser Ser Leu Gln Arg Glu Pro Phe Thr Ile
 65                  70                  75                  80

Ala Gln Gly Lys Gly Gln Lys Leu Cys Glu Ile Glu Arg Ile His Phe
                 85                  90                  95

Phe Leu Ser Lys Lys Lys Thr Asp Glu Leu Arg Asn Leu His Lys Leu
                100                 105                 110

Leu Tyr Asn Arg Pro Gly Thr Val Ser Ser Leu Lys Lys Asn Val Gly
                115                 120                 125

Gln Phe Ser Gly Phe Pro Phe Glu Lys Gly Ser Val Gln Tyr Lys Lys
                130                 135                 140

Lys Glu Glu Met Leu Lys Lys Phe Arg Asn Ala Met Leu Lys Ser Ile
145                 150                 155                 160

Cys Glu Val Leu Asp Leu Glu Arg Ser Gly Val Asn Ser Glu Leu Val
                165                 170                 175

Lys Arg Ile Leu Asn Phe Leu Met His Pro Lys Pro Ser Gly Lys Pro
                180                 185                 190

Leu Pro Lys Ser Lys Lys Thr Cys Ser Lys Gly Ser Lys Lys Glu Arg
                195                 200                 205

Asn Ser Ser Gly Met Ala Arg Lys Ala Lys Arg Thr Lys Cys Pro Glu
            210                 215                 220

Ile Leu Ser Asp Glu Ser Ser Asp Glu Asp Glu Lys Lys Asn Lys
225                 230                 235                 240

Glu Glu Ser Ser Asp Asp Asp Lys Glu Ser Glu Glu Pro Pro
                245                 250                 255

Lys Lys Thr Ala Lys Arg Glu Lys Pro Lys Gln Lys Ala Thr Ser Lys
                260                 265                 270

Ser Lys Lys Ser Val Lys Ser Ala Asn Val Lys Lys Ala Asp Ser Ser
            275                 280                 285

Thr Thr Lys Lys Asn Gln Asn Ser Ser Lys Leu Glu Ser Glu Ser Glu
        290                 295                 300

Asp Ser Ser Asp Asp Glu Pro Leu Ile Lys Lys Leu Lys Pro Pro
305                 310                 315                 320

Thr Asp Glu Glu Leu Lys Glu Thr Ile Lys Lys Leu Leu Ala Ser Ala
                325                 330                 335

Asn Leu Glu Glu Val Thr Met Lys Gln Ile Cys Lys Lys Val Tyr Glu
                340                 345                 350

Asn Tyr Pro Thr Tyr Asp Leu Thr Glu Arg Lys Asp Phe Ile Lys Thr
                355                 360                 365

Thr Val Lys Glu Leu Ile Ser
                370                 375

<210> SEQ ID NO 4
<211> LENGTH: 341
<212> TYPE: PRT
<213> ORGANISM: Homo sapiens

<400> SEQUENCE: 4

Met Ser Ala Ser Ala Pro Ala Ala Glu Gly Glu Gly Thr Pro Thr Gln
 1               5                  10                  15

Pro Ala Ser Glu Lys Glu Pro Glu Met Pro Gly Pro Arg Glu Glu Ser
```

-continued

```
            20                  25                  30
Glu Glu Glu Glu Asp Glu Asp Asp Glu Glu Glu Glu Glu Glu Lys
        35                  40                  45
Gly Lys Gly Gln Lys Leu Cys Glu Ile Glu Arg Ile His Phe Phe Leu
        50                  55                  60
Ser Lys Lys Lys Thr Asp Glu Leu Arg Asn Leu His Lys Leu Leu Tyr
65                  70                  75                  80
Asn Arg Pro Gly Thr Val Ser Ser Leu Lys Lys Asn Val Gly Gln Phe
                85                  90                  95
Ser Gly Phe Pro Phe Glu Lys Gly Ser Val Gln Tyr Lys Lys Lys Glu
                100                 105                 110
Glu Met Leu Lys Lys Phe Arg Asn Ala Met Leu Lys Ser Ile Cys Glu
        115                 120                 125
Val Leu Asp Leu Glu Arg Ser Gly Val Asn Ser Glu Leu Val Lys Arg
        130                 135                 140
Ile Leu Asn Phe Leu Met His Pro Lys Pro Ser Gly Lys Pro Leu Pro
145                 150                 155                 160
Lys Ser Lys Lys Thr Cys Ser Lys Gly Ser Lys Lys Glu Arg Asn Ser
                165                 170                 175
Ser Gly Met Ala Arg Lys Ala Lys Arg Thr Lys Cys Pro Glu Ile Leu
                180                 185                 190
Ser Asp Glu Ser Ser Asp Glu Asp Glu Lys Lys Asn Lys Glu Glu
                195                 200                 205
Ser Ser Asp Asp Glu Asp Lys Glu Ser Glu Glu Glu Pro Pro Lys Lys
        210                 215                 220
Thr Ala Lys Arg Glu Lys Pro Lys Gln Lys Ala Thr Ser Lys Ser Lys
225                 230                 235                 240
Lys Ser Val Lys Ser Ala Asn Val Lys Lys Ala Asp Ser Ser Thr Thr
                245                 250                 255
Lys Lys Asn Gln Asn Ser Ser Lys Lys Glu Ser Glu Ser Glu Asp Ser
                260                 265                 270
Ser Asp Asp Glu Pro Leu Ile Lys Lys Leu Lys Lys Pro Pro Thr Asp
                275                 280                 285
Glu Glu Leu Lys Glu Thr Ile Lys Lys Leu Leu Ala Ser Ala Asn Leu
        290                 295                 300
Glu Glu Val Thr Met Lys Gln Ile Cys Lys Lys Val Tyr Glu Asn Tyr
305                 310                 315                 320
Pro Thr Tyr Asp Leu Thr Glu Arg Lys Asp Phe Ile Lys Thr Thr Val
                325                 330                 335
Lys Glu Leu Ile Ser
                340
```

DEK AS A URINE BASED BIOMARKER FOR BLADDER CANCER

CROSS-REFERENCE TO RELATED APPLICATION

The present application claims the benefit of priority under 35 U.S.C. §119(e) to U.S. Provisional Application Nos. 61/455,405 filed Oct. 20, 2010 and 61/455,406 filed Oct. 20, 2010, the disclosures of which are hereby incorporated by reference in their entireties.

FIELD OF INVENTION

The present invention generally relates to a method of detecting DEK protein in a urine sample. Specifically, the present invention relates to a method of detecting and diagnosing bladder cancer by chemical-induced precipitation of urine proteins, followed by filtration-induced concentration and Western blot analysis to specifically detect DEK protein. The present method permits specific detection of DEK protein in a urine sample, and the presence of DEK is a valuable indicator for bladder cancer.

BACKGROUND OF THE INVENTION

Bladder cancer is a prevalent malignancy in the United States. In 2010, approximately 70,000 newly diagnosed cases of bladder cancer are expected; of those, more than 14,000 are expected to die. According to the American Cancer Society, the five-year survival rate for patients diagnosed with bladder cancer is 98% at stage 0, 88% at stage I, 63% at stage II, 46% at stage III, and 15% at stage IV. These bleak statistics highlight the fact that early detection of bladder cancer is critical for the intervention of the disease. The estimated overall cost per patient from diagnosis of bladder cancer to death is about US $96,000-$187,000; and the total cost amounts to US $3.7 billions.

Early detection of bladder cancer is essential for removing the tumor with preservation of the bladder, avoiding local complications from the tumor such as bleeding or infections, avoiding metastasis and hence improving prognosis and long-term survival. In bladder cancer, ~90% are transitional cell carcinomas, ~5% are squamous cell carcinomas, and ~2% are adenocarcinomas. Of the transitional cell carcinomas, ~75% present as superficial tumors; of which ~50-70% will recur and ~10-20% will progress to invasive bladder tumors. Patients are therefore kept under surveillance for early detection of recurrences.

The current standard methods to detect bladder cancer include cystoscopy and urine cytology. Cystoscopy involves inserting a thin, lighted scope through the patient's urethra into the bladder. It is invasive, unpleasant, and expensive, which in turn leads to poor patient compliance. In addition, cystoscopy often yields false-positive results. Urine cytology is an alternative procedure that involves checking the number and appearance of cells in a urine sample. It has a low sensitivity for detecting small or low-grade bladder tumors.

Numerous urine-based markers have been tested for bladder cancer detection and surveillance. These markers include complement factor H (BTA-Stat/TRAK), nuclear matrix proteins (NMP22), mucin-like antigens, hyaluronic acid, hyaluronidase, survivin, soluble Fas, telomerase and detection of chromosomal aneuploidy and deletion using fluorescence in situ hybridization (UroVysion®). However, none have acceptable sensitivity and specificity as a routine tool for bladder cancer diagnostics and surveillance.

Accordingly, there remains a continuing need for a urine-based test with adequate sensitivity and specificity in the detection and diagnosis of bladder cancer in humans. It would be advantageous to develop a non-invasive and reliable screening method that encourages initial and follow-up screening. The present invention cures all the prior art deficiencies and provides a novel method of detecting DEK protein in urine. The present method provides a high sensitivity and specificity of 79% and 83%, respectively, and can be used as a diagnostic tool to detect bladder cancer in humans.

SUMMARY OF INVENTION

In one aspect, the present invention provides a method of detecting DEK in a urine sample of a human, comprising the steps of: (a) forming a precipitate from a urine sample with a chemical compound selected from the group consisting of acetone, trichloroacetic acid, ethanol, methanol/chloroform and ammonium sulfate; (b) re-suspending said precipitate in a polar solvent to form a solution, said solution has a final volume that is 10-50 fold less than that of said urine sample; (c) concentrating said solution 2-10 fold by filtration; and (d) detecting DEK in said concentrated solution using an anti-DEK antibody in a Western blot assay.

Preferably, the chemical compound is methanol/chloroform or trichloroacetic acid, or acetone. Preferably, the chemical compound and urine sample has a volume to volume ratio of 10:1. More preferably, the chemical compound and urine sample has a volume to volume ratio of 5:1 or 2:1.

Preferably, the polar solvent is tri-ethanol amine. Preferably, the solution in step (b) has a final volume of 15-40 fold less than that of urine sample. Preferably, the solution in step (b) has a final volume of 20 fold less than that of urine sample. More preferably, the concentrated solution in step (c) has a final volume of 5 fold less than that of re-suspended solution.

Preferably, the filtration is performed using a filter that has 3 kD cutoff. The anti-DEK antibody is a monoclonal antibody or a polyclonal antibody. The anti-DEK protein is labeled with horse radish peroxidase.

In another aspect, the present invention provides a method of detecting bladder cancer in a human, comprising the steps of: (a) obtaining a urine sample from a human; (b) forming a precipitate from said urine sample with a chemical compound selected from the group consisting of acetone, trichloroacetic acid, ethanol and ammonium sulfate; (c) re-suspending said precipitate in a polar solvent to form a solution, said solution has a final volume that is 10-50 fold less than that of urine sample; (d) concentrating said solution 2-10 fold by filtration; and (e) detecting DEK in said concentrated solution using an anti-DEK antibody in a Western blot assay, wherein the presence of DEK protein in said urine sample is indicative of a bladder cancer in said human.

Preferably, the bladder cancer is a transitional cell carcinoma.

In yet another aspect, the present invention provides a kit for detecting bladder cancer in a human, comprising: (a) a container for a urine sample; (b) a chemical compound, wherein said chemical compound induces the formation of a precipitate from said urine sample; (c) a polar solvent; (d) a filter with a 3 kD cutoff; and (e) an instruction for the use of said chemical and said filter in preparing said urine sample to allow detection of DEK protein by Western blot assay.

DETAILED DESCRIPTION OF THE INVENTION

The present invention can be better understood from the following description of preferred embodiments, taken in conjunction with the accompanying drawings. It should be apparent to those skilled in the art that the described embodiments of the present invention provided herein are merely exemplary and illustrative and not limiting.

DEFINITIONS

Figure 4:
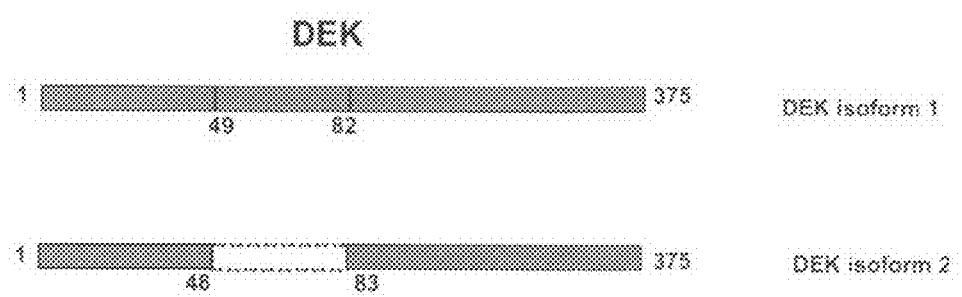
FIG. 4 depicts a graphic representation indicating the two (2) DEK isoforms. Note that while DEK isoform 1 is composed of 375 amino acid residues, DEK isoform 2 lacks the amino acid residues 49-82. The monoclonal antibody (cat no. 610948; BD Bioscience) used in this study recognizes amino acid residues 19-169 and thus only DEK isoform 1, whilst the polyclonal antibody (cat no. A301-335A; Bethyl Laboratories) can recognize both DEK isoform 1 and DEK isoform 2.

The following terms shall have the meanings as defined hereunder:

As used herein, the term "DEK" refers to a protein with one SAP domain. DEK protein binds to cruciform and superhelical DNA and induces positive supercoils into closed circular DNA and involves in splice site selection during mRNA processing. DEK protein encompasses two isoforms (i.e., DEK isoform 1 and DEK isoform 2) (See, FIG. 4). In humans, isoforms 1 and 2 represent splice variants of DEK that are encoded by two corresponding DEK mRNA sequences (NCBI Accession No. NM_003472.3 (SEQ ID NO: 1) and NCBI Accession No. NM_001134709.1 (SEQ ID NOL: 2), respectively) (i.e., the DEK gene is located on chromosome 6p22). NCBI Accession No. for DEK protein isoform 1 is NP_003463.1 (SEQ ID NO: 3). NCBI Accession No. for DEK protein isoform 2 is NP_001128181.1 (SEQ ID NO: 4). The nucleotide sequence as well as the protein sequences are incorporated by reference herein.

As used herein, the term "precipitation" refers to the condensation of a solid in a solution. Such solid is commonly refers to as "precipitate."

As used herein, the term "chemical-induced precipitation" refers to using a chemical compound (e.g., acetone) that causes protein to precipitate from a solution. The precipitated protein is then collected by centrifugation (i.e., pellet). The protein pellet may be re-dissolved in a buffer (i.e., to re-fold protein) to form a solution compatible with downstream protein analysis such as Western blot analysis.

As used herein, the term "acetone" refers to the organic compound with the formula $(CH_3)_2CO$. Acetone is commonly used in inducing precipitation (i.e., causing protein to precipitate from a solution).

As used herein the term "TCA" refers to trichloroacetic acid that is commonly used to precipitate proteins in serum.

As used herein, the term "triethanolamine" refers to an organic chemical compound which contains a tertiary amine and a triol. A triol is a molecule with three alcohol groups. Like other amines, triethanolamine is a strong base due to the lone pair of electrons on the nitrogen atom.

As used herein, the term "filtration" refers to a mechanical or physical operation used for separating solids from fluids by interposing a medium (e.g., filter membrane) through which only the fluid can pass. Oversize solids in the fluid are retained. Filter membrane may have different cut-off pore size, for example, 30 kD or 3 kD cut-off.

As used herein, the term "Western blot assay" refers to an analytical technique used to detect specific proteins in a given sample of tissue homogenate or extract. It utilizes gel electrophoresis to separate either native proteins or denatured proteins by their lengths or 3-D structures. The separated proteins are transferred to a membrane (typically nitrocellulose or PVDF), and are detected using antibodies specific against a target protein.

As used herein, the term "antibody" refers to an immunoglobulin produced by B cells and has structural units of two large heavy chains and two small light chains. There are two general classes of antibody; namely, monoclonal antibody and polyclonal antibody. Monoclonal antibodies (mAb) refer to monospecific antibodies that are the same because they are made by identical immune cells that are all clones of a unique parent cell. Monoclonal antibodies are typically made by fusing myeloma cells with the spleen cells from a mouse that has been immunized with the desired antigen. Polyclonal antibodies are antibodies obtained from different B cells. They are a combination of immunoglobulins secreted against a specific antigen, each identifying a different epitope. Animals frequently used for polyclonal antibody production include goats, guinea pigs, rabbits, horses, sheep and the like. Rabbit is the most commonly used laboratory animal for this purpose.

As used herein, the term "protein" refers to a chain of at least two amino acids. The terms "polypeptide," "peptide," or "protein" are used interchangeably.

As used herein, the term "bladder cancer" refers to a cancerous tumor in the bladder. For purposes of this application, bladder cancer is not intended to be limited to cancer of any specific types (i.e., include many types of cancer in the bladder such as transitional cell carcinoma (TCC), squamous cell carcinoma, adenocarcinoma and combinations thereof).

As used herein, the term "TCC" refers to transitional cell carcinoma (also known as urothelial cell carcinoma or UCC). It is a type of cancer that typically occurs in the urinary system: the kidney, urinary bladder, and accessory organs. It is the most common type of bladder cancer and cancer of the ureter, urethra, and urachus. TCC often arises from the transitional epithelium, a tissue lining the inner surface of these hollow organs.

As used herein, the term "HxTCC" refers to patients that have a previously history of TCC.

As used herein, the term "UroTSA" refers to a cell line isolated from a primary culture of normal human urothelium through immortalization with a construct containing the SV40 large T antigen. It proliferates in serum-containing growth medium as a cell monolayer with little evidence of uroepithelial differentiation.

As used herein, the term "UroTSA DEK-V5" refers to over-expression of DEK in UroTSA cells.

As used herein, the term "UroTSA DEKsh" refers to UroTSA cells that have been transfected with silencing RNA against native DEK mRNA.

As used herein, the term "CAP" refers to human prostate cancer. The term "HxCAP" refers to patients who had previous history of suffering prostate cancer.

As used herein, the term "RCC" refers to renal cell carcinoma (also known as hypernephroma). It is a kidney cancer that originates in the lining of the proximal convoluted tubule. RCC is the most common type of kidney cancer in adults, responsible for approximately 80% of cases. The term "HxRCC" refers to patients who had previous history of suffering renal cell carcinoma.

As used herein, the term "BPH" refers to benign prostatic hyperplasia and is synonymous with "benign enlargement of the prostate" (BEP), and "adenofibromyomatous hyperplasia." All of these diseases are manifested by an increase in size of the prostate, often in middle-aged and elderly men.

The present invention is directed to a novel and non-obvious method to detect DEK protein in a urine sample in humans. The present method comprises the steps of (a) forming a precipitate from a urine sample with a chemical compound selected from the group consisting of acetone, trichloroacetic acid, ethanol, methanol/chloroform, and ammonium sulfate; (b) re-suspending said precipitate in a polar solvent to form a solution, said solution has a final volume that is 10-50 fold less than that of said urine sample; (c) concentrating said solution 2-10 fold by filtration; and (d) detecting DEK in said concentrated solution using an anti-DEK antibody in a Western blot assay.

To the best of the present inventors' knowledge, this represents the first report for detection of DEK in a human urine sample. Using a cDNA microarray system, Sanchez-Carbayo et al. in 2003 reported that DEK gene (among many other genes) is increased in superficial tumors during progression of bladder cancer. Although it is logical to deduce that DEK protein may be presented in urine, no one has successfully documented such a finding and reported the presence of DEK protein in urine. Because DEK is an intracellular protein (i.e., not secreted or released), a mere increase in DEK mRNA in bladder cancer may not correspondingly produce DEK protein in urine. It is also plausible that the dilution of DEK protein in urine exists far below the detection limits of any assay. To date, there is no published literature describing DEK protein expression in multiple low and high grade bladder tumors and in the urine of bladder cancer patients. There are no reports of DEK protein being detected in urine by Western blot assay, or diagnosing/detecting bladder cancer by detecting DEK protein in urine samples. The present method therefore has made a significant improvement over the prior art and clearly documented the presence of DEK in urine (which has not previously known to exist).

Our present finding is surprising because the inventors of this application discovered that the sequential order of concentrating a urine sample is critical for the DEK detection. Specifically, no DEK protein is detectable in urine when a urine sample is concentrated by either chemical-induced precipitation or filtration-induced precipitation alone. DEK protein is also not detectable when a urine sample is first concentrated by filtration followed by a chemically-induced precipitation step. The present inventors discovered that a urine sample must be concentrated first by (i) chemical-induced precipitation, followed by (ii) filtration-induced concentration. The underlying mechanism for this observation is unclear.

Using Western blot assay, the present inventors could not detect DEK protein in either urine pellets or urine supernatants. DEK protein was not detectable even when urines were concentrated by a chemical-induced precipitation method. Consecutive precipitations made no difference. These observations suggest that a mere multi-fold concentration of urine does not lead to a successful detection of DEK. Similarly, when urines were concentrated either by single filtration or consecutive filtration, also failed in DEK detection in urine.

Combination of concentrating first by filtration and then by chemical-induced precipitation was found to be ineffective in detecting DEK protein. Only when the urine sample was first concentrated by chemical-induced precipitation followed by filtration-induced concentration allows DEK protein detectable by Western blot assay.

The present invention provides a unique sequence of concentrating steps that are vital in DEK detection in urine. Without wishing to be bound to a theory, it is believed that a multitude of factors may play a role. These factors include (i) fold concentrations of urine, (ii) DEK protein conformation (i.e., tertiary protein structure of DEK) and (iii) salt concentrations. To be detectable, DEK protein may need a sufficient fold concentration of a urine sample. In chemical-induced precipitation, large amounts of chemical (e.g., acetone) are often needed to achieve the necessary fold concentration. Given this constraint, a single chemical-induced precipitation may not reach the necessary fold concentration. Filtration-induced concentration may cure this deficiency. In the process of chemical-induced precipitation, there may be a slight distort in tertiary protein structure and thus affect Western blot analysis. Filtration-induced concentration, although maintain the optimal protein tertiary structure, suffers from contamination with high salts. Our data with conductivity supports this contention. High salt concentration may affect Western blot assay in DEK detection.

The present inventors also surprisingly discovered a correlation between the presence of DEK protein in urine and detection/diagnosis of bladder cancer in humans. Specifically, the present invention provides a method of detecting bladder cancer in a human, comprising the steps of (a) obtaining a urine sample from a human; (b) forming a precipitate from said urine sample with a chemical compound selected from the group consisting of acetone, trichloroacetic acid, ethanol, methanol/chloroform, and ammonium sulfate; (c) re-suspending said precipitate in a polar solvent to form a solution, said solution has a final volume that is 10-50 fold less than that of urine sample; (d) concentrating said solution 2-10 fold by filtration; and (e) detecting DEK in said concentrated solution using an anti-DEK antibody in a Western blot assay, wherein the presence of DEK protein in said urine sample is an indicative of a bladder cancer in said human.

The present non-invasive method for detecting DEK in urine has an exceedingly high sensitivity (i.e., 79%) and specificity (i.e., 83%) as compared to other urine-based assays. Currently, there are five (5) commercial tests that detect biomarkers of bladder cancer in urine. These include: (i) NMP22 ELISA (detects nuclear mitotic apparatus protein) has 47-100% sensitivity and 60-80% specificity; (ii) BladderChek® dipstick test (detects nuclear mitotic apparatus protein) has 49.5% sensitivity and 87.3% specificity; (iii) BTA-Stat® test (detects complement factor H-related protein) has 50-70% specificity; (iv) urinary bladder cancer test (detects cytokine 8 and cytokine 18 by ELISA) has 56% sensitivity and 97% specificity; and (v) UroVysion® (a fluorescence in situ hybridization (FISH) based assay that detects amplification of chromosomes 3, 7 and 17 and loss of chromosome region 9p21) has 68-81% sensitivity and 79-96% specificity.

Urine may be conveniently collected from a human subject using a suitable container with a sufficient volume capacity for DEK protein assay. Commercially available urine containers may be used. In one embodiment, a urine container may contain a cap to prevent spilling and a means to allow the collected urine sample to be transported. Urine may be stored under appropriate conditions. In one embodiment, the container may be capable of withstanding freezing conditions (e.g., −80° C.). For purposes of the present assay, a sufficient urine volume may range from 15 ml to 75 ml. In one preferred embodiment, urine volume of between 20 ml to 40 ml is adequate.

Time of urine collection is not critical. In one embodiment, urine is collected as first void urine (i.e., in the morning). First void urine is believed to contain a greater amount of proteins, and may therefore increase the ability of detection for urine-based biomarkers. In another embodiment, urine may be collected during daytime or before bedtime.

Freshly collected urine (i.e., urine samples immediately after collection) may be used. Alternatively, frozen urine may be used (i.e., after thawing of frozen urine samples). For purposes of this application, we detect no difference between freshly collected urine and thawed urine. For convenient purposes, collected urine is stored between −20° C. and −80° C. Urine may be conveniently stored for at least 6-month duration.

In one embodiment, a protease inhibitor may be added to a urine sample and in an amount sufficient to prevent potential protein degradation of urine proteins. Suitable protease inhibitor includes, but not limited to, aprotinin, pepstatin, phenylmethanesulfonyl fluoride, chymostatin, and the like. In an alternative embodiment, a cocktail of suitable protease inhibitors may be used. For example, commercially available protease inhibitor cocktail ("Complete Protease Inhibitor Cocktail Tablets") (Roche; cat. no. 11836153001) may be used. In one embodiment, protease inhibitors may be added immediately after urine is collected. In yet an embodiment, protease inhibitors may be added after urine is thawed.

One skilled in the art would know how to optimize the suitable amount of protease inhibitors needed to prevent potential protein degradation in urine. In one embodiment, protease inhibitors are added to achieve a final concentration of 10 µg/ml to 5 mg/ml. In a preferred embodiment, protease inhibitors may be added to achieve a final concentration of 250 mg/ml to 750 µg/ml. In another preferred embodiment, protease inhibitor may be added to achieve a final concentration of 1 mg/ml.

Urine may be turbid which may be a symptom of a bacterial infection. A turbid urine may be caused by crystallization of salts such as calcium phosphate. In one embodiment, potential crude debris present in a turbid urine sample may be cleared prior to the concentrating steps. In one embodiment, collected urine samples may simply be passed through a cloth, paper, tissue and the like. For example, urine may be cleared by passing through a Kimwipe® (Kimberly-Clarke, Dallas, Tex.) prior to the urine concentrating steps.

One aspect of the present invention provides a step of concentrating urine using a chemical compound. Urine may be concentrated by a chemical-induced precipitation. Chemical-induced precipitation generally involves adding a chemical compound to a urine sample to cause urine proteins to form a precipitate. Urine precipitates are visible with a naked eye. Suitable chemical compounds include, without limitation, acetone, trichloroacetic acid, ethanol, methanol/chloroform, ammonium sulfate and the like. In a preferred embodiment, the chemical compound is acetone or tri-chloroacetic acid. Preferably, methanol/chloroform is a solvent mixture comprising methanol and chloroform in a volume to volume ratio of 2:3. Optimal methanol/chloroform volume to volume ratio may be conveniently determined by one of ordinary skilled in the art insofar as they are capable of function to induce urine protein to precipitate.

To aid in urine concentration, chemical compound is used at an amount sufficient to induce the formation of a precipitate. In one embodiment, chemical compound is added to a urine sample to achieve a ratio of chemical compound volume to urine sample volume (vol/vol ratio) of between 10:1 to 2:1. In another embodiment, chemical compound is used at a vol/vol ratio of between 5:1 to 2:1. In a preferred embodiment, the vol/vol ratio is 2:1 (e.g., 50 ml acetone is added to 25 ml urine).

To enhance precipitation formation, it is found that adding ice-cold chemical compound is preferred. In one preferred embodiment, ice-cold acetone is used as the precipitating chemical. In another embodiment, ice-cold acetone is added to the urine sample and the resulting solution continued to be chilled at between −20° C. and −80° C. In yet another embodiment, ice-cold acetone is added to the urine sample and the solution chilled at −40° C.

In one embodiment, the resulting chemical-urine solution (e.g., acetone-urine) is chilled for an additional of 0.5-4 hours to cause the precipitates to be formed. In a preferred embodiment, the solution is chilled for 1-3 hours. In another preferred embodiment, the solution is chilled for 1.5-2 hours.

Methods are known in the art to collect precipitates as pellets after the step of chemical-induced precipitation. For example, a brief centrifugation (e.g., 12,000 rpm, 15 minutes) may be used to collect the precipitated proteins.

Another aspect of the present invention provides a step of further concentrating urine using a filtration method. Prior to the filtration-induced concentration, the pelleted proteins may conveniently be re-suspended in a suitable re-suspension buffer. Without wishing to be bound by a theory, the re-suspension buffer is believed to enhance refolding of the precipitated proteins. Re-suspension may help to restore and reform the precipitated proteins into a proper tertiary protein structure.

Ideally, the re-suspension buffer may match the pH of urine. The pH of urine is close to neutral (pH 7) but can normally vary between 4.4 and 8. A diet high in citrus, vegetables, or dairy can increase urine pH. Some drugs can increase urine pH, including acetazolamide, potassium citrate, and sodium bicarbonate. On the other hand, a diet high in meat or cranberries can decrease urine pH. Drugs that can decrease urine pH include ammonium chloride, chlorothiazide diuretics, and methenamine mandelate. In one embodiment, the re-suspension buffer has a pH of between 5-9. More preferably, the re-suspension buffer has a pH of between 6-8. More preferably, the re-suspension buffer has a pH of 7.5.

One skilled in the art would recognize the use of common buffers to maintain pH of the re-suspension buffer. A buffer solution is an aqueous solution consisting of a mixture of a weak acid and its conjugate base or a weak base and its conjugate acid. Buffer solutions are used as a means of keeping pH at a nearly constant value in a wide variety of chemical applications. Exemplary common buffer includes triethanolamine, TRIS, HEPES, MOPS, and the like. Preferably, the re-suspension buffer is isotonic.

In one embodiment, the re-suspension buffer is an organic chemical compound which is both a tertiary amine and a triol such as triethanolamine. Preferably, the re-suspension buffer contains 10 mM triethanolamine. In another embodiment, the re-suspension buffer may include a sugar to enhance tonicity. Exemplary sugar includes, but not limited to, sucrose. Preferably, the re-suspension buffer contains 250 mM sucrose. An exemplary re-suspension buffer is a solution of 10 mM triethanolamine and 250 mM sucrose.

The pelleted proteins are re-suspended at a minimal volume that is much less than the original urine sample volume. One of skilled in the art would recognize a minimum optimal volume in re-suspending the pellet proteins. In one embodiment, the pelleted protein is re-suspended in a volume of re-suspension buffer of 500 µl. The volume of the re-suspension buffer may range from 5-50 fold less than that of the original urine sample. Preferably, the volume of the re-suspension buffer ranges from 20-40 fold less than the original urine sample volume. More preferably, the volume of the re-suspended is 30 fold less than the original urine sample volume (e.g., pelleted proteins from 60 ml urine is re-suspended in 500 µl re-suspension buffer).

Re-suspended concentrated urine is further concentrated. In one aspect, the present invention provides a step of concentrating urine by filtration. Filtration-induced concentration may be accomplished through the use of spin filter concentration units. Examples of commercially available spin-filter concentration units include units sold under the tradenames Microcon®, Centricon® and Centriprep®.

In one embodiment, the spin filter has a molecular weight cut-off of between 1 kD and 40 kD. In another embodiment, the spin filter has a molecular weight cut-off of 3 kD. In another embodiment, the spin filter has a molecular weight cut-off of 30 kD.

Ideally, filtration-induced concentration is used to achieve an increase of concentration between 2-fold to 10-fold. In one embodiment, concentration is increased between 4-fold to 8-fold. In a preferred embodiment, concentration is increased 5-fold.

Protein concentrations of urine samples may be conveniently quantified by methods that are known to the art including assays that are commercially available. For example, one commercially available kit is the BCA assay kit (Pierce, Thermo Fisher Scientific, Rockford, Ill.).

In one aspect, the present invention provides an assay to detect DEK protein present in the concentrated urine samples. In one embodiment, protein present in the filtration-concentrated sample is adjusted to a level of 10-1,000 µg/ml. Preferably, the protein concentration in the filtration-concentrated sample is 100 µg/ml.

DEK protein may be detected using standard protein detection assays that are known in the art. These assays include, but not limited to, Western blot analysis, ELISA, radioimmunoassay, dot-blot assay, and the like. Preferably, DEK protein is detected by Western blot analysis.

After urine samples are treated (i.e., subject to chemical-induced precipitation and filtration-induced concentration), the proteins are separated using SDS-PAGE gel electrophoresis. The technology of SDS-PAGE gel electrophoresis is well known in the art. Approximately 5 µg to 100 µg of total protein is run on a SDS-PAGE gel. Preferably, 10 µg to 75 µg of total protein is used. More preferably, 25 µg of total protein is used. The conditions for SDS-PAGE gel electrophoresis can be conveniently optimized by one skilled in the art. In one embodiment, SDS-PAGE gel is run at 100V for 90 min of 400 mA for 90 minutes. Optimally, gel electrophoresis may be performed under denaturing conditions. SDS-PAGE gel electrophoresis conditions are well known by those skilled in the art and can be conveniently optimized.

Following gel electrophoresis, the proteins present in the gels may be transferred onto a suitable solid surface such as nitrocellulose paper, nylon membrane, PVDF membrane and the like. Preferably, PVDF membrane is used. The conditions for protein transfer after SDS-PAGE gel electrophoresis may be optimized by one skilled in the art.

Western blot may be used to detect DEK protein in the concentrated urine (after SDS-PAGE). A first antibody specific for the protein of interest (e.g., DEK) is employed. The first antibody may be either a monoclonal antibody or polyclonal antibody. Antibodies against the protein biomarker can be prepared using standard protocols or obtained from commercial sources. Techniques for preparing mouse monoclonal antibodies or goat or rabbit polyclonal antibodies (or fragments thereof) are well known in the art.

Membrane may be incubated with a blocking solution before the incubation with the first antibody. Blocking solution may include agents that reduce non-specific binding of antibody. For example, blocking solution may include 5% skim milk in PBST (0.1% Tween-20).

Bound proteins (e.g., 10-100 µg) on the membrane are incubated with a first antibody in a solution. In one embodiment, the first antibody is used at a concentration of 0.2-2 µg/mL. Preferably, the first antibody is used at a concentration of 1 µg/mL.

Incubation conditions may be optimized to maximize the binding of the first antibody with the bound biomarker proteins. In one embodiment, the incubation time is 1-6 hours. In a preferred embodiment, the incubation time is 2 hours.

After incubation with the first antibody, unbound antibody may be conveniently removed by washing. In one embodiment, the washing solution may include PBST.

Protein biomarker-first antibody complex (e.g., DEK-anti-DEK antibody) may be detected by incubation with a second antibody that is specific for the first antibody. The second antibody may be a monoclonal antibody or a polyclonal antibody (e.g., mouse, rabbit, or goat). In one embodiment, the second antibody may carry a label which may be a directly detectable label or may be a component of a signal-generating system. In another embodiment, the second antibody is a goat anti-rabbit antibody or goat anti-mouse antibody that is labeled with a peroxidase. Such labeled antibodies and systems are well known in the art.

Direct detectable label or signal-generating systems are well known in the field of immunoassay. Labeling of a second antibody with a detectable label or a component of a signal-generating system may be carried out by techniques well known in the art. Examples of direct labels include radioactive labels, enzymes, fluorescent and chemiluminescent substances. Radioactive labels include $^{124}I$, $^{125}I$, $^{128}I$, $^{131}I$, and the like. A fluorescent label includes fluorescein, rhodamine, rhodamine derivatives, and the like. Chemiluminescent substances include ECL chemiluminescent.

In another aspect, the present invention provides a method of detecting and diagnosing bladder cancer. This is accomplished by obtaining and testing a urine sample and detecting the presence of DEK protein in the urine sample by the detection method provided herein. The presence of DEK protein in the urine sample indicates that the patient tested is suffering from bladder cancer. Thus, the present invention provides an efficient, non-invasive method for the detection and diagnosis of bladder cancer by detecting DEK protein in a urine sample.

Our Western blot assay results suggest that urine contains only DEK isoform 2 in individuals suffering from bladder cancer. In our assay, we used a monoclonal anti-DEK antibody that specifically recognize DEK isoform 1 (but not DEK isoform 2) (i.e., the antibody was specifically recognizes the amino acid residues 19-169 and thus bind only to DEK isoform 1 but not DEK iso form 2). The polyclonal anti-DEK antibody that was used recognizes both DEK isoforms. Because both monoclonal and polyclonal anti-DEK antibodies recognized DEK proteins in both bladder cancer cell culture and bladder cancer tissue samples, this implies that DEK iso form 1 and DEK isoform 2 are present in these cells and tissues.

However, only the polyclonal anti-DEK antibody (but not the monoclonal anti-DEK antibody) recognized DEK protein in urine samples from patients suffering bladder cancer, this suggests urine contains DEK isoform 2, but not DEK iso form 1.

Kits

Another aspect of the invention is to provide a kit which may be used to detect DEK protein in urine. The kit according to the present invention includes a set of antibodies (i.e., a first antibody and a second antibody) that are specific for DEK protein. The kit also contains reagents (e.g., precipitating chemicals such as acetone or TCA) for treating the urine sample so as to enable DEK protein to be detected from the sample.

Kits provided herein may also include instructions, such as a package insert having instructions thereon, for using the reagents to prepare and steps in concentrating a urine sample. Such instructions may be for using the reagents to prepare the urine sample to specifically allow detection of DEK protein from the urine. In another embodiment, the instructions are directed to the use of antibodies (either monoclonal or polyclonal) that recognize and bind to DEK protein.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1

Western Blot Detection of DEK Protein in Bladder Cell Lines

In this series of studies, we optimized the detection of DEK protein in a biological sample (e.g., urine) using Western blot assay. We tested cell lysate extracts obtained from four (4) bladder cancer cell lines (i.e., RT-4, 5637, T-24 and TCCSUP) and examined their DEK protein expression. These cells were chosen to represent different stages of bladder cancer. In addition, we tested cell extracts from bladder epithelial cells transformed with SV-40 T-antigen (i.e., UroTSA), progenitor human epithelial cells (i.e., HBEP cells), and differentiated HBEP cells for their DEK protein expression. Note that HBEP cells were treated with 1 mM calcium chloride to prevent cycling in growth media.

Cell extracts from 1×10⁷ cells were obtained using RIPA buffer (i.e., 25 mM Tris-HCl (pH 7.6), 150 mM NaCl, 1% NP-40, 1% sodium deoxycholate, and 0.1% SDS). Protein was quantified using a BCA assay kit (Pierce, Thermo Fisher Scientific, Rockford, Ill.). Cell lysates extracts were further concentrated to a concentration of between 4 and 8 µg/µl. 30 µg of the cell extracts were used in the Western blot analysis using an anti-DEK antibody (e.g., an anti-DEK monoclonal antibody; cat #610948) (BD Bioscience, San Jose, Calif.).

Figure 1:
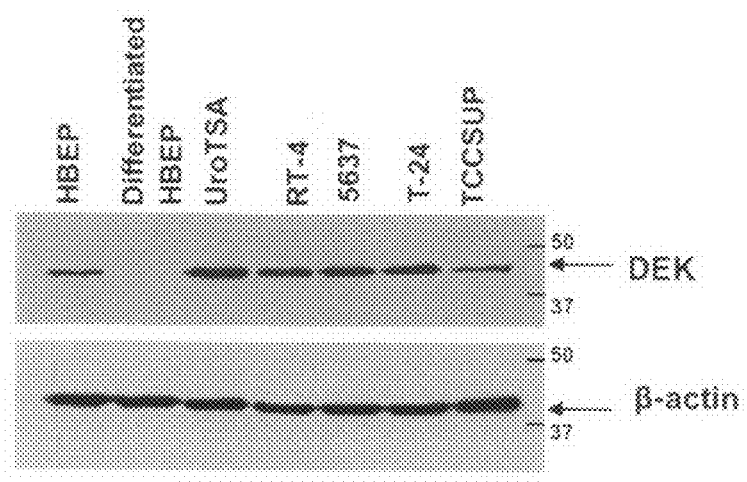
FIG. 1 depicts the expression of DEK protein in undifferentiated bladder epithelial cell line (i.e., HBEP), differentiated HBEP, a transformed epithelial cell line (i.e., UroTSA), and four (4) bladder cancer cell lines (i.e., RT-4, 5637, T-24 and TCCSUP) in a Western blot assay. β-actin serves as a positive control protein.

FIG. 1 shows a Western blot demonstrating the presence of DEK protein expressed in four (4) bladder cancer cell lines (i.e., RT-4, 5637, T-24 and TCCSUP) as well as the UroTSA and undifferentiated HBEP cells. In this Western blot analysis, we used a monoclonal anti-DEK antibody (cat. no. 610948) (BD Bioscience, San Jose, Calif.). Note that DEK protein has a molecular size of ~43 kD. DEK protein was not detectable in differentiated (i.e., non-cancer) HBEP cells. β-actin served as a loading control. In another Western blot analysis, we used a polyclonal anti-DEK antibody (cat. no. A-301-335A) (Bethyl Labs, Montgomery, Tex.). Similar to that in monoclonal antibody study, we observed a similar profile in DEK protein expression in these cells (data not shown).

Thus, we have developed a Western blot assay that is sensitive and specific in detecting DEK protein expression using cell lysates extracts obtained from bladder cancer cell lines, using either a monoclonal anti-DEK antibody or a polyclonal anti-DEK antibody.

Example 2

Western Blot Fails to Detect DEK Protein in Cultured Media

In this study, we examined if DEK protein can be released from bladder cancer cells (i.e., secreted from cells). To do so, we first collected cultured media from two (2) bladder cancer cell lines (i.e., T-24 and 5637) and then examined DEK protein expression in these cultured media. One (1) ml of cultured media was collected and briefly centrifuged (3,000 rpm, 5 min) to remove any cellular debris. The cultured media was subsequently concentrated to 50-fold (i.e., from 500 µl to 10 µl) using a Microcon® 3K filter (Millipore, Billerica, Mass.). The entire 10 µl of the concentrated cultured media sample was loaded in a Western blot assay. DEK protein was examined using a polyclonal anti-DEK antibody (cat. no. A-301-335A) (Bethyl Labs., Montgomery, Tex.). UroTSA (10 µg) whole cell lysate was used as a control.

Figure 2:
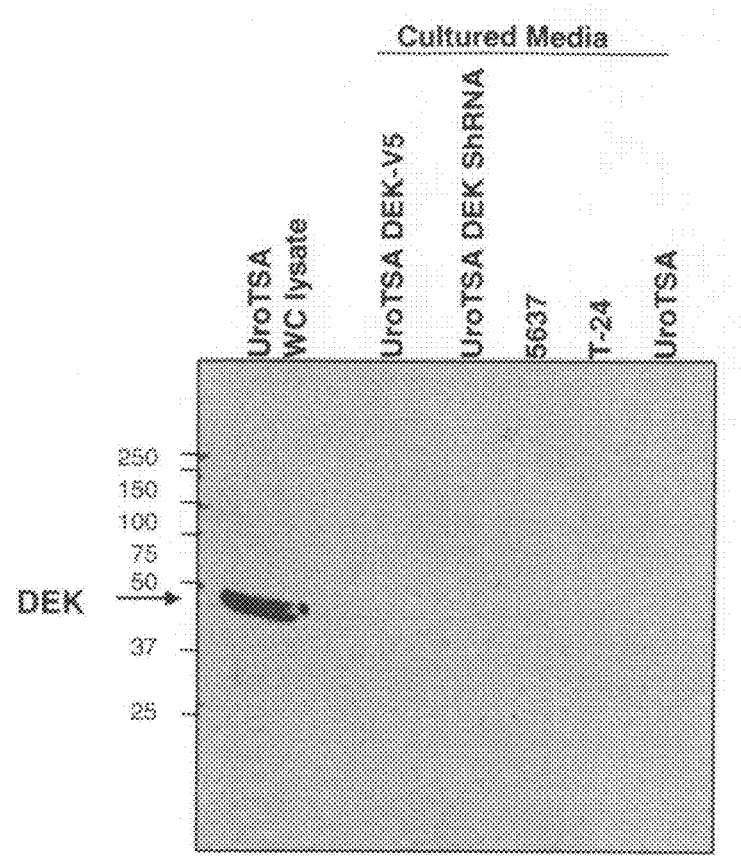
FIG. 2 depicts the expression of DEK protein in the cultured media from five (5) different cultured cell lines in a Western blot assay. These include: (i) a transformed epithelial cell line (i.e., UroTSA) transfected with DEK-V5; (ii) UroTSA hosting shRNA against DEK (i.e., DEK knockdown); (iii) bladder cancer cell line 5637; (iv) bladder cancer cell line T-24; and (v) UroTSA. Whole cell lysates from UroTSA (i.e., WC lysates of UroTSA) serves as a positive control.

FIG. 2 shows that DEK protein was not detectable in the cultured media of the two (2) bladder cancer cell lines (i.e., T-24 and 5637). DEK protein was not detectable in the cultured media from the transformed bladder epithelial cells (i.e., UroTSA) and from bladder epithelial cells that were over-expressing DEK protein (UroTSA DEK-V5). This data suggest that DEK protein is neither secreted nor released from bladder cancer cells. As a negative control, we transfected DEK shRNA (i.e., small hairpin RNA against DEK) in UroTSA cells in order to shut down DEK protein expression. No detectable DEK protein was found in the cultured media from UroTSA DEK shRNA, confirming that DEK protein may not be released from bladder cancer cells.

Example 3

Western Blot Detection of DEK Protein in Bladder Tissues

In this study, we examined if our Western blot assay (see Example 1) could detect DEK protein in bladder tissues obtained from human subjects (e.g., bladder cancer patients or healthy individuals).

Twenty-seven (27) bladder tumor tissue samples were obtained from patients who suffered from low and high grade transitional cell carcinoma (TCC). For comparison, twenty-seven (27) normal bladder tissue samples were obtained from the adjacent sites of the same individuals. Tissue lysate extracts were prepared using RIPA buffer (as described above) and the tissue extracts were prepared to a protein concentration of 2-10 µg/µl. Protein concentration of the tissue lysates extracts was determined using a BCA assay kit (Pierce, Thermo Fisher Scientific, Rockford, Ill.). ~50 µg of the tissue lysates extracts from each sample was analyzed for their DEK protein expression in our Western blot assay, using a monoclonal anti-DEK antibody (i.e., cat. no. 610948). In some Western blot analysis, we used a polyclonal anti-DEK antibody (cat. no. A-301-335A) (Bethyl Labs, Montgomery, Tex.) and observed the same DEK protein expression. 10 µg of the UroTSA cell lysates was used as a control.

Figure 3:
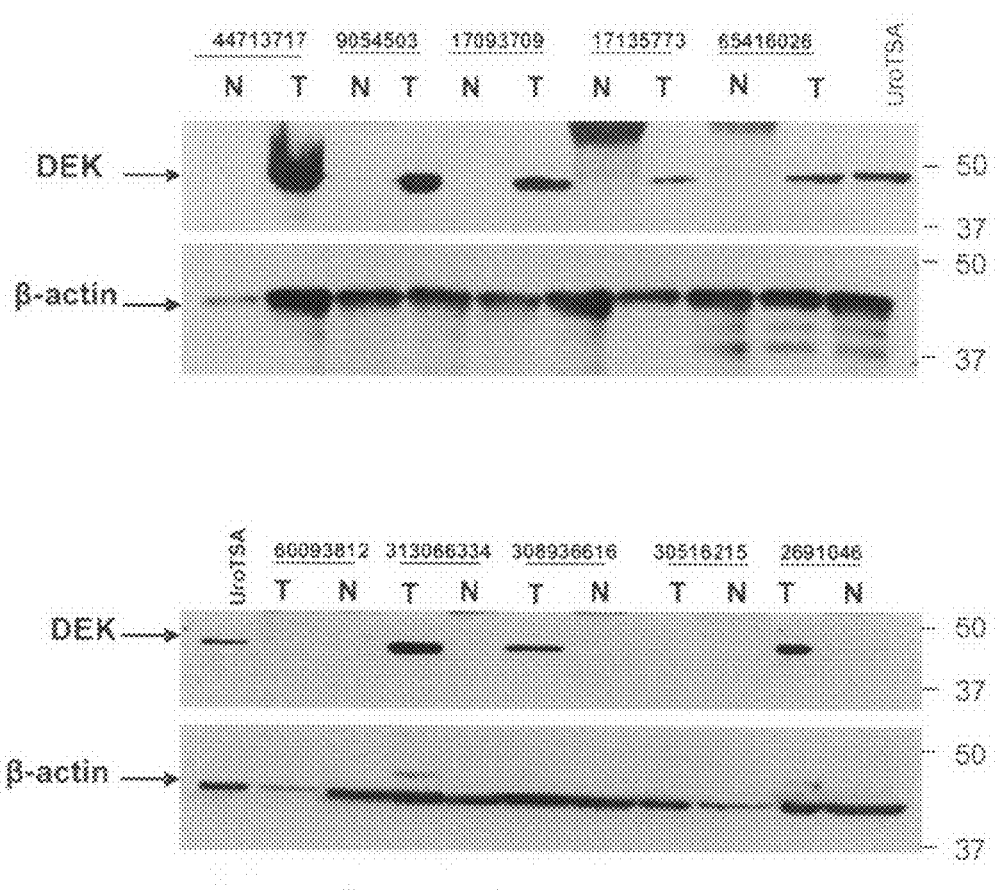
FIG. 3 depicts the expression of DEK protein of bladder tumor tissues (i.e., T) from ten (10) bladder cancer patients in a Western blot assay. Adjacent tissues (i.e., N) from the same patients were used as a comparison. UroTSA serves as a control cell line. β-actin serves as a positive control protein.

FIG. 3 shows the Western blot of the DEK protein in ten (10) representative bladder tumor tissues using the monoclonal anti-DEK antibody. In total, we have examined twenty-seven (27) bladder tissue samples. Out of these bladder tissue samples, DEK protein expression was detected in twenty-two (22) bladder tumor tissues. The bladder tumor was clinically diagnosed as transitional cell carcinoma (TCC). A summary of the DEK protein expression in all these bladder tissues are provided in Table 1. Note that DEK protein expression was detected in both low-grade TCC and high-grade TCC. DEK protein was not detectable in the adjacent normal bladder tissues, indicating high specificity. Our polyclonal ant-DEK antibody was employed in some Western blot analysis and we have confirmed a similar DEK protein expression in these bladder tumor tissues.

TABLE 1

DEK Protein Expression in Bladder Tumor Tissues

| | | | DEK Protein Expression | |
| --- | --- | --- | --- | --- |
| Tissue Samples | Cancer Staging | Grade | TCC Tissues | Normal Adjacent Tissues |
| 17135773 | High | T2 | + | − |
| 2691046 | High | T2 | ++++++ | − |
| 30516215 | High | T2 Squamous Differentiation | − | − |
| 44713717 | High | T2 | ++++ | − |
| 52203387 | High | T1 | ++++++ | − |
| 65416026 | High | T1 | ++ | − |
| A00309103 | High | T3a | +++ | − |
| B0087901 | High | TX | ++++ | − |
| B01712101 | High | Tx | − | − |
| E00061103 | High | T1 | − | − |
| E00397102 | High | | ++ | − |
| E00749102 | High | T3 | ++ | − |
| 17093709 | Low | TA | +++ | − |
| 308936616 | Low | TA | ++++ | − |
| 313066334 | Low | T1 | ++++++ | − |
| 314593377 | Low | TA | ++++ | − |
| 42070185 | Low | TA | ++++++ | − |
| 53976239 | Low | T1 | ++++++ | − |

TABLE 1-continued

DEK Protein Expression in Bladder Tumor Tissues

| Tissue Samples | Cancer Staging | Grade | TCC Tissues | Normal Adjacent Tissues |
|---|---|---|---|---|
| 60093812 | Low | T1 Squamous Differentiation | – | – |
| 8875254 | Low | TA | + | – |
| 9054503 | Low | TA | +++ | – |
| A00050109 | X | T1 | ++++ | – |
| A00491105 | X | T2b | – | – |
| A00903104 | X | T2a | ++++ | – |
| E00019101 | X | TX | + | – |
| E0028719 | X | T4 | ++ | – |
| E00300105 | X | T1 | ++++ | – |
| 42012815 | X | Inflammation | – | – |

In sum, we have developed a Western blot assay for detecting DEK protein expression. Using this assay, we have found DEK protein expression in bladder tissues from individuals suffering from low-grade and high-grade bladder cancer. The data further show that DEK protein can be found to present in bladder tissues as early as stage 0a (i.e., Ta) in bladder cancer. Note that DEK protein is not expressed in normal healthy tissues, indicating high specificity.

DEK Isoforms and Antibody Recognition—

So far, we have used two (2) anti-DEK antibodies in the Western blot analysis for bladder cancer cell extracts and tissue extracts. The first antibody was a monoclonal anti-DEK antibody (cat. no. 610948) obtained from BD Bioscience (San Jose, Calif.). This monoclonal antibody was raised using synthetic peptides corresponding to the amino acid residues 19-169 of the DEK isoform 1 (See, FIG. 4). The second antibody was a polyclonal anti-DEK antibody (cat. no. A-301-335A) available from Bethyl Labs (Montgomery, Tex.). This polyclonal antibody was raised using synthetic peptides corresponding to amino acid residues 325-375 of the DEK isoform 1 (See, FIG. 4). DEK protein is known to encompass two (2) isoforms (namely; DEK isoform 1 and DEK isoform 2). DEK isoform 2 differs from DEK isoform 1 by missing the amino acid residues 49-82. It is noted that our monoclonal antibody can recognize DEK isoform 1 (but not DEK iso form 2), while our polyclonal antibody can recognize both DEK isoforms. (See, FIG. 4).

We observed DEK protein expression in both bladder cancer cell line extracts and bladder tumor tissue extracts. Because our monoclonal anti-DEK antibody can only recognize DEK isoform 1 but not isoform 2 and our polyclonal anti-DEK antibody recognizes both iso forms, we concluded that bladder cancer cell lines and bladder tumor tissues express both DEK isoform 1 and DEK isoform 2.

Example 4

Western Blot Detection of DEK Protein in Urine

Urine samples (in aliquots of 25 ml) were collected in the presence of various protease inhibitors (e.g., aprotinin, pepstatin, phenylmethanesulfonyl fluoride, chymostatin, etc) at a concentration sufficient to inhibit protease activity (e.g., 1 mg/ml) to avoid potential DEK protein degradation. In this particular study, we used a protease inhibitor cocktail (Roche, Indianapolis, Ind.). Urine samples could be used immediately after collection or may be stored at −80° C. For the sake of convenience, most of our studies employed frozen urine samples. Prior to Western blot analysis, frozen urine samples were thawed by leaving the samples at room temperature for 1-2 hours.

We examined if our Western blot assay could detect DEK protein in human urine. We obtained urine samples from four (4) patients suffering from bladder cancer and one (1) healthy patient.

a) Urine Pellet

It is possible that bladder cancer cells slough off from the bladder lining into urine. To determine this possibility, we obtained urine pellet (containing potential bladder cancer cells). To do so, we centrifuged the thawed urine (i.e., 5,000 rpm for 5 min.) to obtain the urine pellets. The urine pellets were re-suspended in 1 ml of ice cold PBS. Urine pellets were solubilized by lysing the pellets in 40 μl of Lysis Buffer B (i.e., 50 mM Tris (pH 7.4), 250 mM NaCl, 0.5% NP-40, 1% Triton X-100). Urine pellet lysates were further incubated on ice for an additional 10 minutes. The lysates samples were centrifuged at 12,000 rpm for 10 minutes. Total protein in the urine lysates was quantified using a BCA assay kit (Pierce, Thermo Fisher Scientific, Rockford, Ill.) and protein concentration for each sample was adjusted to a range of 0.5-1.5 μg/μl. 30 μl of urine pellet lysate was analyzed for DEK protein expression in solubilized urine pellets using our Western blot assay with the polyclonal anti-DEK antibody (cat. no. A-301-335A) (detailed in Example 1). 10 μg of UroTSA cell lysate served as a control. 5 μl of the urine pellet lysate corresponding to 5 μg protein was resolved on 10% SDS-PAGE gel and stained with Coomassie blue.

Figure 5:
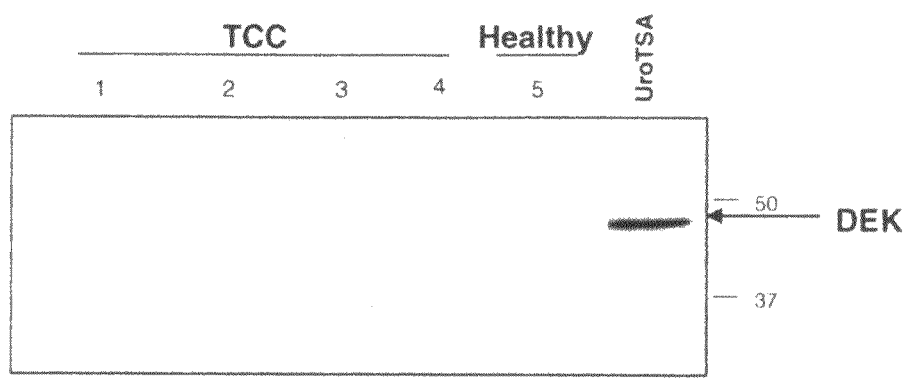
FIG. 5 depicts the expression of DEK protein in urine pellets obtained from four (4) bladder cancer patients (i.e., TCC) and a healthy individual in a Western blot assay. UroTSA serves as a control.
Figure 6:
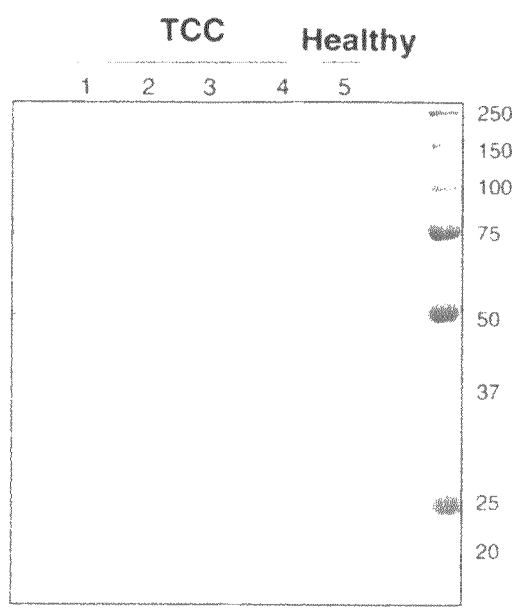
FIG. 6 depicts a Coomassie-blue stained 10% SDS-PAGE gel of proteins resolved from urine pellet lysates from four (4) bladder cancer patients (i.e., TCC) as well as a healthy individual.

FIG. 5 shows that DEK protein was not detected in the urine pellets of the patients suffering from bladder cancer or in the urine pellets of healthy patients using our Western blot assay. No protein was detected in the urine pellets of four (4) of the five (5) samples. (See, FIG. 6). This data suggests that DEK protein cannot be detected from the urine pellets by our Western blot assay.

b) Urine Supernatant

To determine if DEK protein may be secreted or released into urine, we tested neat urine supernatant for DEK protein expression using our Western blot assay. In this study, urine was obtained from two (2) patients suffering from transitional cell carcinoma (TCC) and from two (2) healthy subjects.

50 μl of neat urine supernatant from each of the two (2) patients suffering from TCC and the two (2) healthy patients was run in a Western blot assay using our polyclonal anti-DEK antibodies (cat. no. A-301-335A). 10 μg of cell lysate from T-24 bladder cancer cells served as a control.

Figure 7:
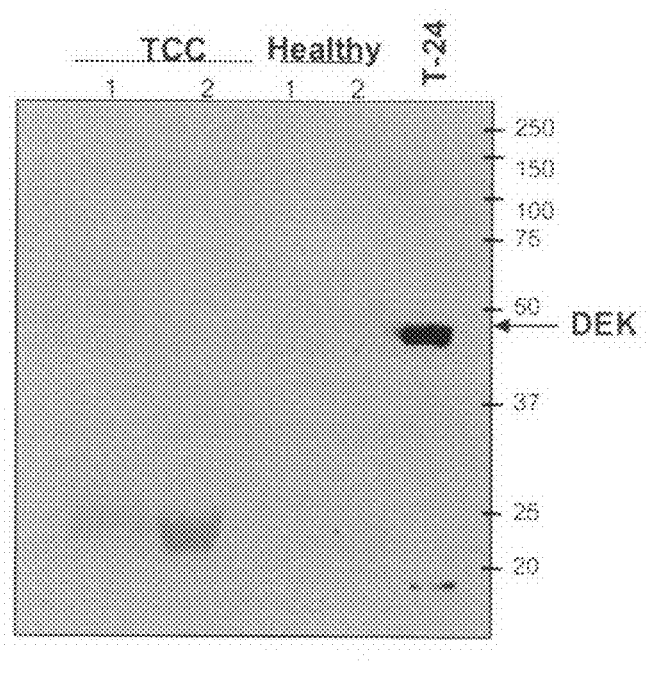
FIG. 7 depicts the expression of DEK protein in urine supernatant (neat) in a Western blot assay obtained from two (2) bladder cancer patients (i.e., TCC) and two (2) healthy individuals. Bladder cancer cell line T-24 serves as a control.

FIG. 7 shows that DEK protein was not detected in the neat urine supernatant of the two (2) patients suffering from TCC as well as from the two (2) healthy individuals.

To verify if there were indeed proteins present in the urine supernatants, we resolve total proteins on a 10% SDS-PAGE gel followed by staining with Coomassie blue.

Figure 8:
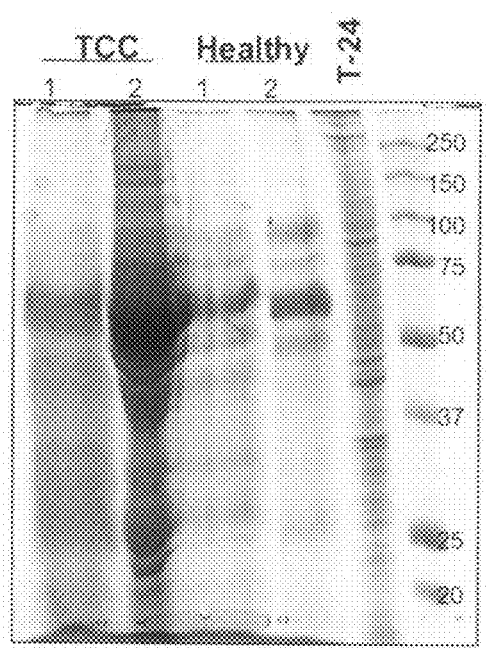
FIG. 8 depicts Coomassie-blue stained 10% SDS-PAGE gel of proteins resolved from the urine supernatant (neat) from two (2) bladder cancer patients (i.e., TCC), two (2) healthy individuals and bladder cancer cell T-24.

FIG. 8 clearly show that there were abundant proteins present in each of the neat urine supernatants tested. Thus, we concluded that DEK protein could not be detected in neat urine supernatants from bladder cancer patients using Western blot assay.

Example 5

Western Blot Detection of DEK Protein in Concentrated Urine (by Filtration Method)

It is plausible that the neat urine may contain DEK protein that is in small amounts beyond the sensitivity of detection by our Western blot assay. To enhance DEK protein concentration in urine samples, we concentrated urine samples 10-fold using filtration method.

Urine samples from three (3) patients were used in this concentration study: (i) a patient suffering with bladder cancer (i.e., TCC), (ii) a patient with a history of prostate cancer (i.e., HxCAP), and (iii) a patient with a history of renal cell carcinoma (i.e., HxRCC).

500 µl of the thawed urine sample was concentrated 10-fold (i.e., to a final volume of 50 µl) using a Microcon® 3K filter (Millipore, Billerica, Mass.) (10,000 rpm, 10 min. at room temp.). All of the 50 µl of the 10-fold concentrated urine sample was analyzed for DEK protein expression on a Western blot assay, using the polyclonal anti-DEK antibody (cat. no. A-301-335A). UroTSA whole cell lysate (10 µg) served as a control.

Figure 9:
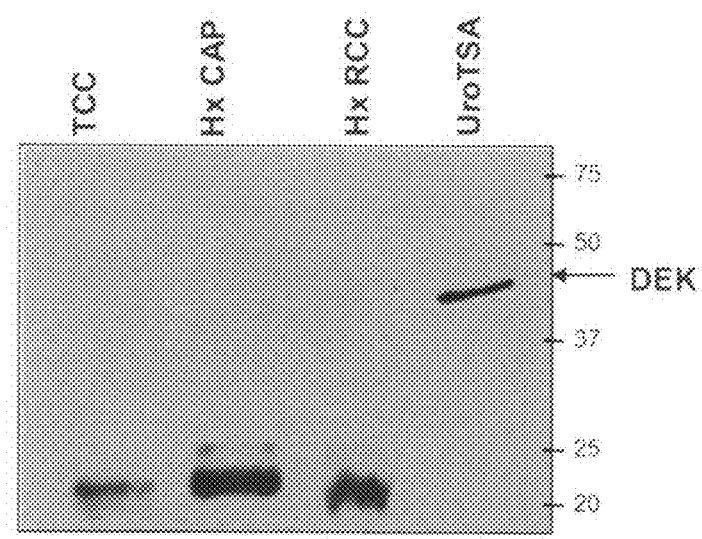
FIG. 9 depicts the expression of DEK protein in urine samples that were concentrated using a 3 kD filter as detected in a Western blot assay. Urine samples were obtained from one (1) patient with bladder cancer (i.e., TCC), one (1) patient with a history of prostate cancer (i.e., HxCAP), and one (1) patient with a history of renal cell carcinoma (i.e., HxRCC). UroTSA cell lysate was used as a control.

FIG. 9 shows that DEK protein was not detectable by Western blot assay even following 10-fold concentration of the urine samples by filtration method. This suggests that concentrating urine (e.g., by 10-fold) using filtration does not permit detecting DEK protein expression by our Western blot assay.

Example 6

Western Blot Detection of DEK Protein in Concentrated Urine (Chemical-Induced Precipitation)

We employed a different method to concentrate urine samples. In this study, we performed a chemical-induced precipitation method. Acetone was used as a chemical compound to cause protein precipitation in urine. Single acetone precipitation on urine samples was performed.

Potential coarse debris present in the thawed urine (25 ml) was removed by passing the thawed urine through a Kimwipe® (Kimberly-Clarke Corp., Irving, Tex.). To induce precipitation, ice-cold acetone (volume to volume ratio of acetone to urine was 2.5:1) was added to the urine sample. Chemical-induced precipitation was permitted to occur by incubating the acetone-treated urine at −20° C. for 1 hour.

Acetone-induced precipitates were obtained by a brief centrifugation of the acetone-treated urine (12,000 rpm, 10 min). The precipitates were re-suspended in a buffer containing sucrose (sucrose buffer) (i.e., 10 mM triethanol amine containing 250 mM sucrose) in 500 µl volume. This volume of sucrose buffer was found to be effective in re-suspending the precipitates to solution (i.e., completely dissolve the residues). Therefore, the acetone-induced precipitation caused the urine proteins to increase to a 50-fold concentration.

We obtained urine samples from four (4) different patient groups: (i) a patient with renal cell carcinoma (i.e., RCC); (ii) a patient with prostate cancer (i.e., CAP), (iii) a patient with benign enlarged prostate (i.e., BPH); and, (iv) a patient with transitional cell carcinoma (i.e., TCC).

The total proteins in the sucrose-buffer re-suspended urine precipitates were quantified using a BCA assay kit (Pierce, Thermo Fisher Scientific, Rockford, Ill.). 50 µg of protein (i.e., 50-80 µl) was used to run on a Western blot assay using our polyclonal anti-DEK antibody (cat. no. A-301-335A). UroTSA whole cell lysate (10 µg) served as a control.

Figure 10:
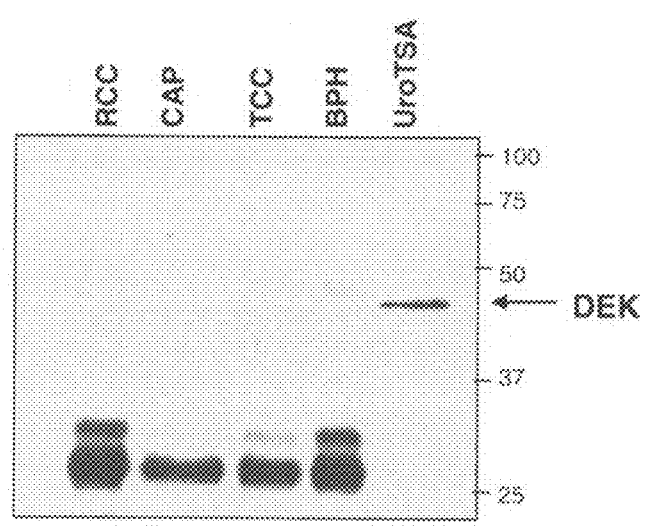
FIG. 10 depicts the expression of DEK protein in urine samples that were treated with acetone to obtain precipitates. The re-suspended precipitates were subjected to a Western blot assay to detect DEK protein. Urine samples were obtained from one (1) patient with renal cell carcinoma (i.e., RCC), one (1) patient with prostate cancer (i.e., CAP), one (1) patient with bladder cancer (i.e., TCC), and one (1) patient with a benign enlarged prostate (i.e., BPH). UroTSA cell lysate was used as a control.

FIG. 10 shows that DEK protein was not detected by our Western blot assay in the concentrated urine samples (e.g., 50-fold concentrated urine by acetone precipitation).

In parallel, 20 µg of acetone-precipitated urine proteins were resolved on a 10% SDS-PAGE gel and stained with Coomassie stain to test for the presence of protein in the samples.

Figure 11:
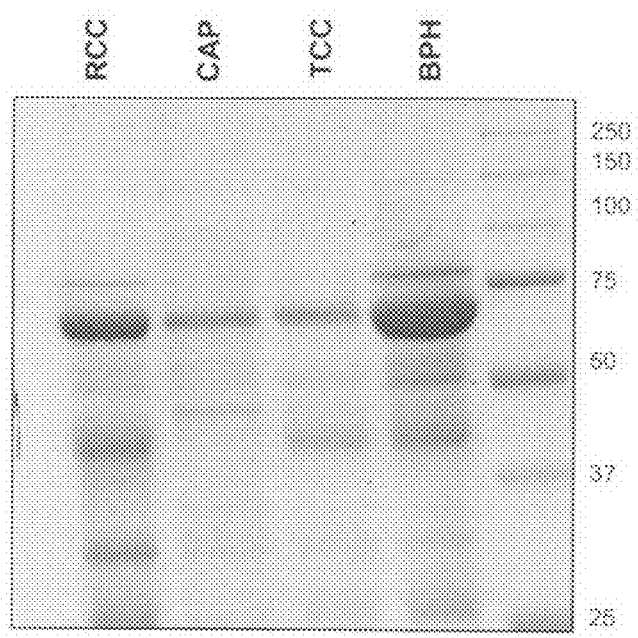
FIG. 11 depicts Coomassie-blue stained 10% SDS-PAGE gel of the proteins resolved from acetone precipitated urines from one (1) patient with renal cell carcinoma (i.e., RCC), one (1) patient with prostate cancer (i.e., CAP), one (1) patient with bladder cancer (i.e., TCC), one (1) patient with benign enlarged prostate (i.e., BPH) and UroTSA cell lysates.

FIG. 11 clearly shows that proteins were present in each of the tested concentrated urine samples. This result indicates that acetone-induced concentration of urine proteins (i.e., by 50-fold) is not sufficient to permit detection of DEK protein expression by our Western blot assay.

Example 7

Western Blot Detection of DEK Protein in Consecutively Chemical-Induced Precipitation of Urine We further assessed if multiple chemical-induced precipitations (e.g., acetone) would permit detection of DEK protein expression by our Western blot assay. We repeated the same experiment as detailed above in Example 6. After the single acetone precipitation, and re-suspension of the precipitates in 500 µl of sucrose buffer.

10 ml PBS was added to the re-suspended precipitates to form PBS solution prior to performing a second acetone precipitation. To the 10 ml PBS solution we added a 2.5× volume of acetone (i.e., 25 ml ice-cold acetone) (vol/vol of acetone to PBS solution was 2.5:1).

The final pellet was re-suspended in 600 µl of sucrose buffer (10 mM Triethanolamine and 250 mM Sucrose). The amount of protein in each sample was quantified using a BCA assay kit (Pierce, Thermo Fisher Scientific, Rockford, Ill.). 50 µg of protein (50-80 µl) was run on a Western blot assay.

We tested ~100 µg total protein of the single acetone precipitated samples and 100 µg total proteins from the double acetone precipitated samples by Western blot analysis using polyclonal anti-DEK antibody. UroTSA cell lysate (10 µg) served as a control.

Figure 12:
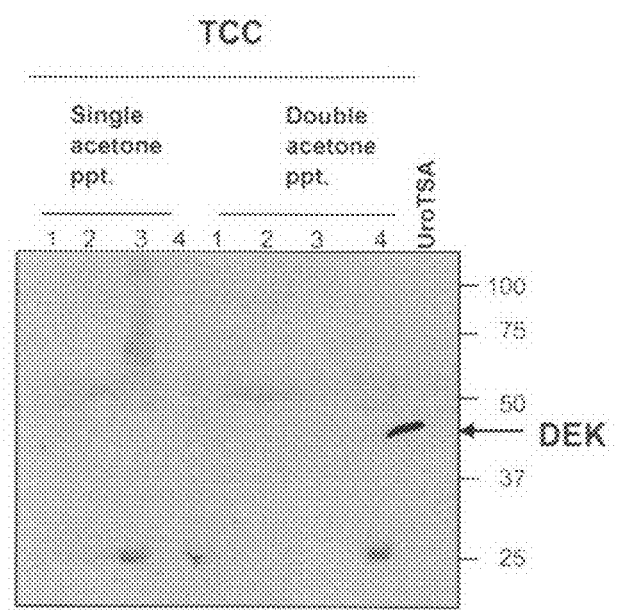
FIG. 12 depicts the expression of DEK protein as detected by Western blot assay in urine samples that were treated with acetone to obtain precipitates. Urine samples were obtained from four (4) bladder cancer patients (i.e., TCC). Samples were tested after a single protein precipitation with acetone (i.e., single acetone ppt.) and after a second protein precipitation with acetone (i.e., double acetone ppt.).
Figure 13:
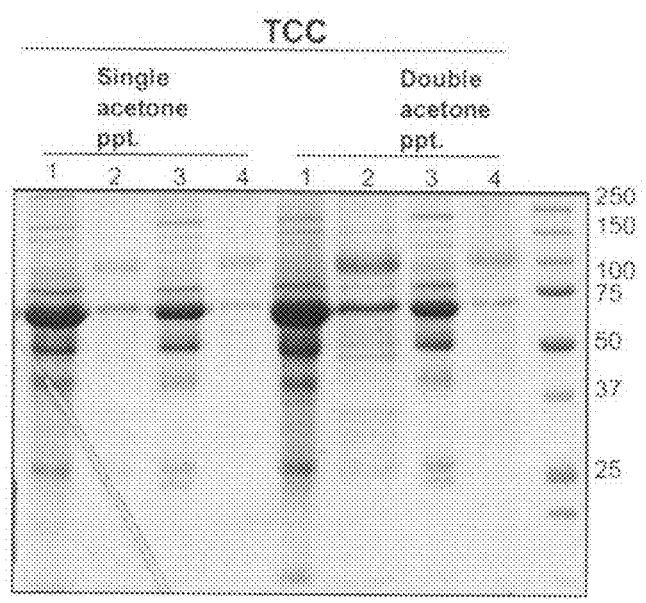
FIG. 13 depicts Coomassie-blue stained 10% SDS-PAGE gel of the proteins resolved from urine samples subjected to single (i.e., Single acetone ppt.) and double acetone precipitation (i.e., Double acetone ppt.). Urine samples were obtained from four (4) bladder cancer patients (i.e., TCC).

FIG. 12 demonstrates that DEK protein was not detected in any of the tested samples, whether single or double acetone precipitated. Proteins were, however, detected in all samples run on a 10% SDS-PAGE gel and stained with Coomassie blue (See, FIG. 13). This suggests that multiple chemical-induced precipitations of urine samples do not permit detection of DEK protein by Western blot assay.

Example 8

Western Blot Detection of DEK Protein in Concentrated Urine After Filtration-Induced Concentration Followed by Chemical-Induced Precipitation In this example, we examined if a combination of filtration-induced concentration method and chemical-induced precipitation method would further lead to concentration of urine samples and thus would permit DEK protein detection by our Western blot assay.

In this series of study, we concentrated urine samples by: (i) first subjecting the urine samples to filtration-induced concentration protocol (i.e., concentrating urine samples with a 30K Amicon® column), and (ii) then subjecting the filter-concentrated urine samples to a chemical-induced precipitation (i.e., a single acetone precipitation).

Urine samples from two (2) transitional cell carcinoma (i.e., TCC) patients were used in this study. 15 ml urine was filtered with a 30K Amicon® column by spinning the column at 6,000 rpm for 30 min. This filtration-induced concentration method caused the urine sample to undergo a 30-fold increase in concentration (i.e., from 15 ml to 500 μl). The 500 μl samples were re-suspended in 10 ml phosphate buffer saline (PBS).

The 10 ml re-suspended solution were then treated with ice-cold acetone (i.e., 2.5 volume of acetone was added to the solution to cause precipitation) (See, acetone-induced precipitation protocols as detailed in Example 6). The chemical-induced precipitation further resulted in an additional 20-fold increase in concentration. Protein was quantified using BCA assay.

Figure 14:
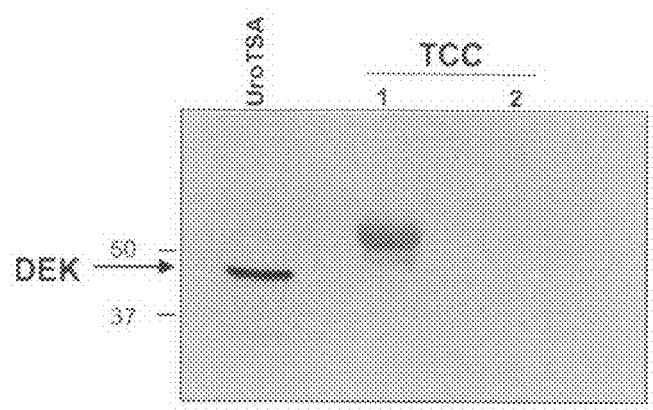
FIG. 14 depicts the expression of DEK protein in urine treated first by filtration with a 30 kD cut-off membrane filter followed by acetone precipitation as detected by Western blot assay. Urine was obtained from two (2) patients suffering from bladder cancer (i.e., TCC). UroTSA cell lysate was used as a control.

50 μg (~90 μl) was analyzed for the presence of DEK protein in our Western blot assay using the polyclonal anti-DEK antibody (cat. no. A-301-335A). UroTSA cell lysate (10 μg) was used as a control. FIG. 14 shows that DEK protein was not detected by our Western blot assay in either of the two TCC samples.

Figure 15:
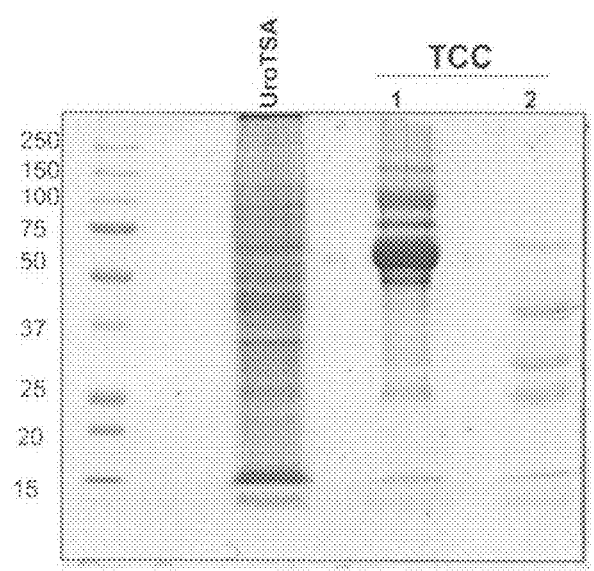
FIG. 15 depicts Coomassie-blue stained 10% SDS-PAGE gel of the proteins resolved from urine treated by filtration with a 30 kD cut-off membrane filter followed by acetone precipitation. Samples from two (2) patients suffering from bladder cancer (i.e., TCC) and UroTSA cell lysate were tested.

20 μg of each sample was run on a 10% SDS-PAGE gel to test for the presence of protein in the samples. Proteins were detected in the samples as shown by the Coomassie blue stained 10% SDS-PAGE gel. (See, FIG. 15). This data indicates that concentrating urine by first filtration-induced method followed by chemical-induced method (i.e., acetone precipitation) still does not permit DEK protein detection by Western blot assay (despite a 600-fold increase in protein concentration of urine).

Example 9

Western Blot Detection of DEK Protein in Concentrated Urine After Filtration-Induced Concentration Followed by Three Consecutive Chemical-Induced Precipitations In this example, we examined if a combination of filtration-induced concentration method and consecutive chemical-induced precipitations may further concentrate urine samples and thus permit detection of DEK protein expression in our Western blot assay.

In this experiment, urine samples were: (i) first concentrated by filtration protocol (i.e., concentrating urine samples with a 30K Amicon® column), and (ii) then concentrated by a consecutive (3×) chemical-induced precipitations (i.e., acetone precipitation). Specifically, urine sample (15 ml) from one (1) patient with bladder cancer (i.e., TCC) was concentrated with a 30K Amicon® column (spinning at 6,000 rpm for 30 min.). This filtration-induced concentration method caused the urine sample to undergo a 100-fold increase in concentration (i.e., from 15 ml to 150 μl). The 100-fold concentrated urine sample was diluted with 10 ml PBS to form a solution (PBS solution).

Then, the PBS solution (containing the concentrated urine sample after the filtration step) was then subjected to three (3) consecutive chemical-induced precipitations (i.e., acetone precipitation). Specifically, ice-cold acetone (volume to volume of acetone to concentrated urine sample was 4:1) were added to the samples to cause precipitation (i.e., adding 40 ml acetone to the 10 ml PBS solution). The mixture was chilled for an additional one (1) hour at −20° C. The mixture was centrifuged (12,000 rpm for 5 min.) to collect the precipitates. The resulting precipitates was re-suspended in 500 μl of buffer A (50 mM Tris (pH 7.4), 0.5% NP-40, 1% Triton X-100). Note that buffer A contains a low salt content (preferably <100 mM NaCl) because a high salt concentration (e.g., >250 mM NaCl) is shown to adversely affect protein migration in a Western blot gel.

The acetone precipitation was repeated (i.e., a total of three times). Each time, the precipitates were re-suspended in 10 ml PBS prior to acetone addition. The final acetone precipitates were re-suspended in 50 μl of buffer A. The present combination of filtration-induced concentration method and consecutive 3× chemical-induced precipitations resulted in an increase of concentration of a total of 300-fold.

Figure 16:
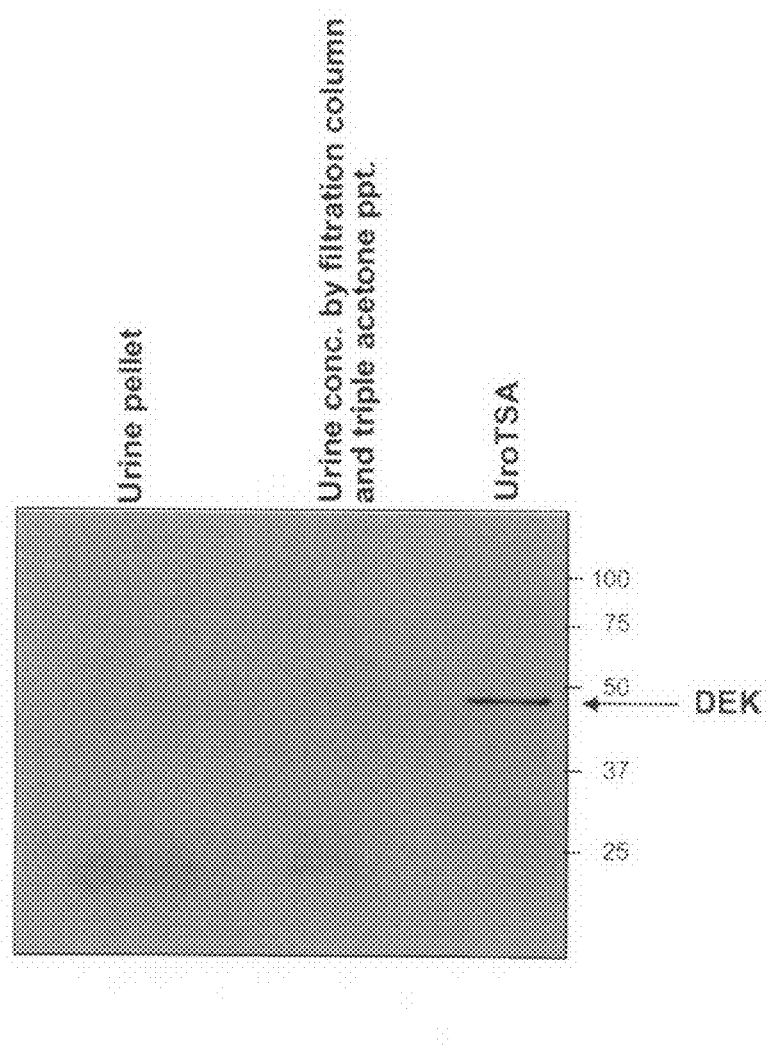
FIG. 16 depicts the expression of DEK protein in urine treated first by filtration with a 30 kD cut-off membrane filter followed by consecutive triple (3×) acetone precipitations. Urine was obtained from one (1) patient suffering from bladder cancer (i.e., TCC). Expression of DEK protein in these urines was tested by Western blot assay. UroTSA cell lysate was used as a control.

50 μl of the sample was analyzed in our Western blot assay using the polyclonal anti-DEK antibody. FIG. 16 shows that DEK protein was still not detected by our Western blot assay, despite a 300-fold increase in concentration. Similarly, no DEK protein was detected in the urine pellet (FIG. 16).

Example 10

Western Blot Detection of DEK Protein in Concentrated Urine After Chemical-Induced Precipitation Followed by Filtration-Induced Concentration In this example, we examined if the sequence of the concentration protocols may permit the detection of DEK protein expression in our Western blot assay.

To test this theory, we employed urine samples from seven (7) patients suffering from transitional cell carcinoma (i.e., TCC), six (6) patients suffering from prostate cancer (i.e., CAP), five (5) patients suffering from renal cell carcinoma (i.e., RCC) and one (1) patient with a history of transitional cell carcinoma (i.e., HxTCC).

Contrary to the sequence order of the concentration protocols detailed in Example 9, the urine samples were: (i) first concentrated by a chemical-induced precipitation method (i.e., a single acetone precipitation), and (ii) then concentrated the urine samples by a filtration method (i.e., concentrating urine samples with a 3K Microcon® filter.

Specifically, 20 ml of urine was treated with two (2) volumes (i.e., 40 ml) of ice-cold acetone. Samples were chilled for an additional one (1) hour at −20° C. and centrifuged briefly (12,000 rpm for 10 min.) to collect the precipitates (i.e., to obtain a pellet). The pellet was re-suspended in 2 ml of sucrose buffer (i.e., 10 mM Tri ethanol amine and 250 mM sucrose). This acetone-induced precipitation caused an increase in concentration of urine proteins of 10-fold (i.e., from 20 ml to 2 ml).

400 μl of the re-suspended urine sample was further concentrated using a 3K Microcon® filter. Samples were spun at 10,000 rpm for 10 minutes to obtain a final volume of ~100 μl (i.e., an additional 4-fold increase in concentration). Therefore, the combination of acetone-induced precipitation followed by filtration caused a total of 40-fold increase in concentration of urine. 30 μl of concentrated urine sample was analyzed by our Western blot assay using polyclonal anti-DEK antibody.

Figure 17:
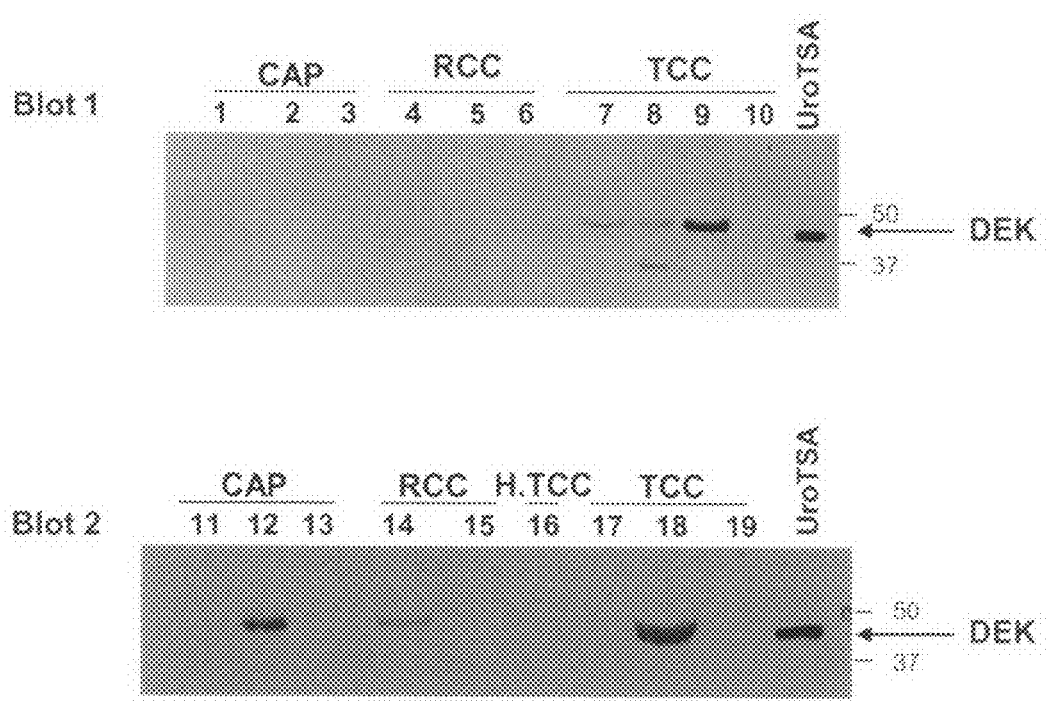
FIG. 17 depicts the expression of DEK protein in urine concentrated first by acetone precipitation and then filtered with a 3 kD cut-off membrane filter as detected in a Western blot assay. Urine was obtained from six (6) patients suffering from prostate cancer (i.e., CAP), five (5) patients suffering from renal cell carcinoma (i.e., RCC), seven (7) patients suffering from transitional cell carcinoma (i.e., TCC) and one (1) patient with a history of transitional cell carcinoma (H.TCC). UroTSA cell lysate was used as a control.

FIG. 17 shows DEK protein expression in the concentrated urine samples. DEK protein expression was clearly detected in four (4) of the seven (7) TCC patient samples (i.e., lanes 7, 8, 9, 18), in one (1) of the five (5) RCC patient samples (i.e., lane 14), and in one (1) of the six (6) CAP patient samples (i.e., lane 12). DEK protein was not detected in the patient with a history of TCC (i.e., lane 16).

These results were unexpected and surprising. And they represent the first report that DEK protein could be detected in urine samples of bladder cancer patients using a Western blot assay. The success of DEK protein detection resides on the unique sequence of urine concentrations (i.e., first by a chemical-induced precipitation method followed by a filtration method).

Example 11

Patient Study—Western Blot Detection of DEK Protein Expression in Urine From Bladder Cancer Patients Using the sequential concentration protocols detailed in Example 10, we next analyzed DEK protein expression in bladder cancer patient urine samples. This study is aimed to provide a correlation between urine DEK protein expression and the development of bladder cancer in humans.

Urine was collected from eight (8) patient groups: (i) fourteen (14) patients with varying grades of transitional cell carcinoma (i.e., TCC), (ii) eight (8) patients with prostate cancer (i.e., CAP), (iii) four (4) patients with renal cancer (i.e., RCC), (iv) three (3) nonmalignant urologenital disease (including one (1) patient suffering from cystitis and (2) suffering from chronic inflammation), (v) one (1) patient suffering from renal oncocytoma, (vi) one (1) patient suffering from renal cystic nephroma, (vii) one (1) patient that had undergone radical cystemectomy (no tumor found), and (viii) five (5) healthy individuals.

A total of thirty-six (36) urine samples (20 ml each) from the eight (8) patient groups were evaluated. Urine was sequentially concentrated using the acetone-precipitation method followed by the filtration method as described in Example 10 (above). The concentrated urine was then analyzed using our Western blot assay with the polyclonal anti-DEK antibody.

Table 2 summarizes the DEK protein expression in our Western blot assay. In brief, we detected DEK protein expression in the urine of fifteen (15) of the nineteen (19) bladder cancer patients (i.e., TCC). DEK protein expression was not detected in the urine of healthy individuals. In addition, DEK protein expression was not detected in the urine of twelve (12) of the sixteen (16) individuals that were suffering from a non-bladder cancer ailment (e.g., CAP, RCC, chronic inflammation, cystitis).

TABLE 2

DEK Protein in Urine Samples from Bladder Cancer Patients

| Urine Sample Source | DEK Western Blot |
|---|---|
| TCC Ta low grade (I) | positive |
| TCC Ta low grade (I-II) | positive |
| TCC Ta low grade (I) with squamous differentiation | positive |
| TCC Ta low grade (II) | negative |
| TCC Ta low grade (I) | positive |
| TCC Ta low grade (I) | positive |
| TCC Ta low grade (I-II) | positive |
| TCC Ta low grade (I) with squamous differentiation | positive |
| TCC Ta low grade (I) | positive |
| TCC Ta low grade (I) | negative |
| TCC T1 low grade | negative |
| TCC T1 high grade with papillary + solid pattern | positive |
| TCC T1 high grade(III) + CIS with solid pattern | positive |
| TCC T1 high grade | positive |
| TCC T2 high grade + CIS | positive |
| TCC T2 high grade | positive |
| TCC T2 high grade (III) | positive |

TABLE 2-continued

DEK Protein in Urine Samples from Bladder Cancer Patients

| Urine Sample Source | DEK Western Blot |
|---|---|
| TCC T2 high grade (III) & papillary RCC type1 | negative |
| TCC T2 high grade (III) | positive |
| TCC inconclusive pathology | negative |
| Chronic inflammation (history of TCC) | positive |
| No tumor on radical cystectomy (history of TCC) | negative |
| CAP | negative |
| CAP | positive |
| CAP | negative |
| CAP | negative |
| CAP | negative |
| CAP | negative |
| CAP | negative |
| RCC | negative |
| RCC | negative |
| RCC | positive |
| RCC | positive |
| Renal oncocytoma | negative |
| Renal cystic nephroma | negative |
| Cystitis | negative |
| Chronic inflammation | negative |
| Healthy | negative |
| Healthy | negative |
| Healthy | negative |
| Healthy | negative |
| Healthy | negative |
| Healthy | negative |

Figure 18:
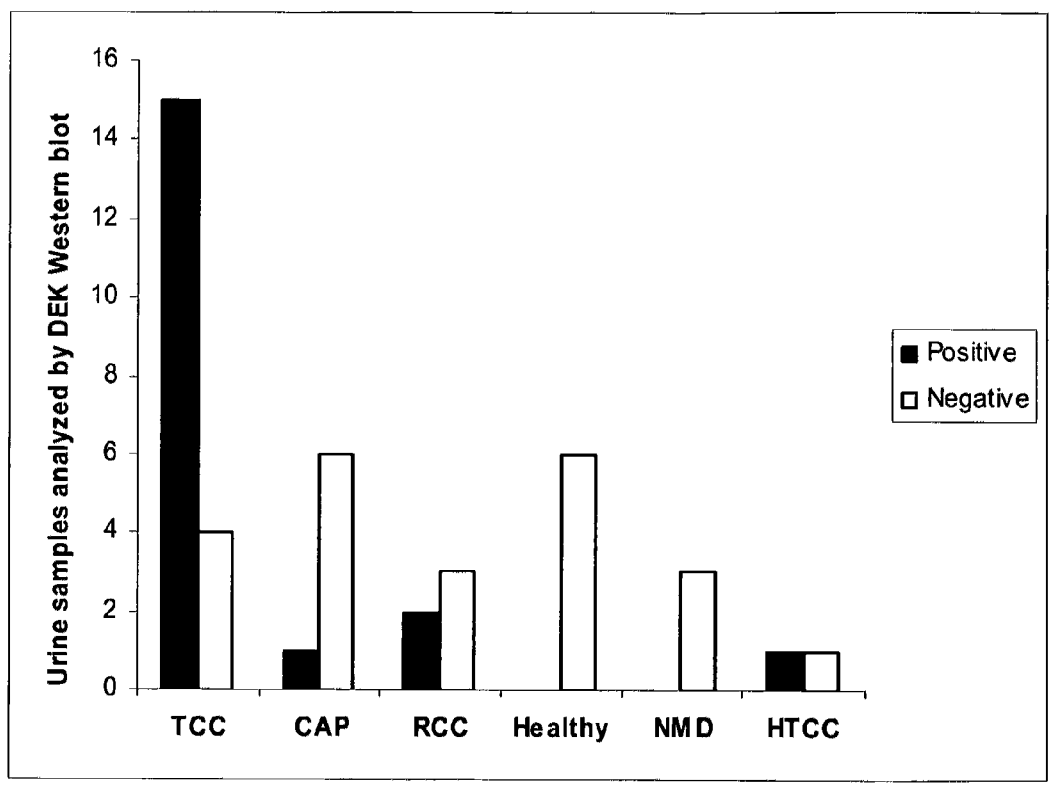
FIG. 18 depicts the number of urine samples per patient groups (i.e., TCC, CAP, RCC, NMD, and HTCC) that tested positive for DEK in urine samples by a Western blot assay.

FIG. 18 shows the graphical representation of DEK Western blot results presented in Table 2.

Altogether, this data demonstrates that DEK protein is present in the urine of bladder cancer patients. It is detected in both low grade and high grade bladder cancer patients. DEK protein is not found either in the urine of healthy individuals or in the urine of non-bladder cancer patients, indicating specificity of DEK protein as a biomarker for bladder cancer.

Overall, the present method of detecting DEK protein in urine has a high sensitivity (79%) and specificity (83%). The presence of DEK protein in urine is a viable method for detecting and diagnosing bladder cancer in humans.

Example 12

Conductivity of Urine Samples

In this series of studies, we examined the potential mechanistic basis for whether filtration or acetone-induced precipitation of urine may change the salt concentrations in the urine. It is our contention that an alteration of salt concentrations in urine may affect the outcome of DEK protein detection in our Western blot analysis (e.g., imparting a conformational change in DEK protein).

To do so, we measured the conductivity of the urine before and after the filtration and acetone-induced precipitation. It has been established that conductivity of urine is an indication of salt concentrations (e.g., high conductivity means a high salt concentration and low conductivity means a low salt concentration).

We processed urine samples as described in Examples 4b, 5, 6, 7, 8, 9, 10 and 11. 50 µl of each sample was added to 5 ml of de-ionized water. Conductivity was determined using a conductivity meter (Traceable Expanded-Range Conductivity Meter, VWR, model no. 89094-958). Conductivity results are summarized in Table 3.

TABLE 3

Conductivity Values for Urine Samples

| Processing Methods | Conductivity (μS/cm) |
| --- | --- |
| None (Example 4b: Neat Urine) | 132 |
| Microcon ® 3K Filtration (Example 5) | 146 |
| Single Acetone Precipitation (Example 6) | 110 |
| Consecutive Acetone Precipitations (Example 7) | 185 |
| 30K Amicon ® Filtration followed by a Single Acetone Precipitation (Example 8) | 114.9 |
| 30K Amicon ® Filtration followed by Three Consecutive Acetone Precipitations (Example 9) | 27.6 |
| Acetone Precipitation followed by Microcon ® 3K Filtration (Example 10) | 170.6 |

Conductivity in urine samples was decreased after acetone precipitation (1×) (i.e., Example 6), after filtration with a 30K Amicon® column followed by a single acetone precipitation (i.e., Example 8), and after filtration followed by a consecutive (3×) acetone precipitations (i.e., Example 9).

Conductivity in urine samples was increased after filtration with a Microcon® 3K column (i.e., Example 5), after consecutive (3×) acetone precipitation (i.e., Example 7), and after acetone precipitation followed by filtration (i.e., Example 10).

Because DEK protein is only found to be present in the urine after acetone-induced precipitation followed by filtration, the conductivity data (in Table 3) does not provide a mechanistic basis for our finding. There is no clear pattern or trend of urine conductivity between filtration and acetone-induced precipitation.

Experimental Methods and Procedures

1. Cell Lines:

Human bladder cancer cell lines (e.g., T-24 and RT-4) were maintained in McCoy's 5A medium supplemented with 10% fetal bovine serum (FBS). Human bladder cancer cell lines (e.g., 5637 and TCCSUP) were maintained in RPMI supplemented with 10% FBS. SV-40 transformed human bladder urothelium cell line (i.e., UroTSA cell line) was maintained in DMEM medium supplemented with 10% FBS. Human bladder epithelium progenitor cell line (i.e., HBEP) (obtained from CELL N TEC®, Stauffacherstr, Bern, Switzerland) was maintained in CnT-58 medium. Differentiated epithelial cells were maintained in accordance with the manufacturer's protocol. All cell lines were maintained at 37° C. in 5% $CO_2$.

2. Whole Cell Lysates from Cell Lines:

Prior to cell lysis, cultured cells were washed with 10 ml of cold PBS. Cells were lysed using 1 ml of RIPA buffer (150 mM NaCl, 0.01 M sodium pyrophosphate, 10 mM EDTA, 10 mM sodium fluoride, 50 mM Tris ph 8.8, 0.1% SDS, 12.8 mM deoxycholic acid, 10% glycerol, 1% NP-40) supplemented with protease inhibitors (Roche, Indianapolis, Ind.) at a concentration of 1 μg/μl. Lysed cells were scraped and transferred to 1.5 ml centrifuge tube and centrifuged at 14,000 rpm for 10 min. to collect supernatant (i.e., whole cell lysates).

3. Urine and Tissue Sample Collections:

Urine samples were obtained from patients with bladder cancer (i.e., TCC), prostate cancer (i.e., CAP), renal cancer (i.e., RCC), non-malignant urogenital diseases and healthy individuals. Urine samples (~20-50 ml aliquots) were collected from patients in Wolfson Medical Center (Israel). Urine samples were stored in the presence of protease inhibitors (Complete Protease Inhibitor Tablets, Roche, Indianapolis, Ind.) at 1 μg/μl and maintained at −20° C.

Frozen, cold cut tissue samples from bladder tumor and adjacent normal tissues were obtained from patients from Wolfson Medical Center (Israel) as well as from ABS Analytical Biological Services Inc. (US).

4. Tissue Extracts from Tissue Samples:

Cold cut tissue samples were collected and immediately frozen upon removal. Samples were shipped on dried ice and stored at −80° C. To obtain tissue extract, cold cut frozen tissue samples were homogenized in RIPA buffer (400 μl) using a mortar and pestle. Homogenized tissue was centrifuged at 14,000 rpm at 4° C. for 20 min and supernatant was saved for downstream analysis. The amount of protein in each sample was quantified using a BCA assay kit (Pierce, Thermo Fisher Scientific, Rockford, Ill.).

5. Urine Pellet Lysates:

To obtain lysates from urine pellet, urine was first centrifuged at 3,000 rpm for 5 minutes to obtain a pellet. The pellet was then washed three times with 10 ml PBS and then lysed in 100 μl lysis buffer B (150 mM NaCl, 0.2% TritonX-100 and 10 mM Tris pH 7.4). 50 μl of the urine pellet lysate was used in the Western blot assay or in protein detection gels.

6. Chemical-Induced Precipitation of Protein in Urine:

Fresh urine samples were used in chemical induced protein precipitation. Alternatively, frozen urine samples were thawed at room temperature prior to protein precipitation. Chemicals used in protein precipitation included acetone, ethanol, TCA, and methanol-chloroform. These chemicals were used (preferably maintained at −20° C. when in use) in an amount sufficient to induce formation of precipitates in urine. The precipitates were then re-suspended in a sucrose buffer (10 mM triethanolamine and 250 mM sucrose).

7. Preparation of DEK Knockdown Cell Lines:

293FT cells (cat. no. R700-07, Invitrogen, Carlsbad, Calif.) were used in the preparation of DEK-ShRNA lentivirus particles. A DEK shRNA (TGCTGTTGACAGT-GAGCGCGCACATTTGGC TTACAGTAAATAGT-GAAGCCACAGATGTATTTACTGTAAGCCAAATGTG-CTT GCCTACTGCCTCGGA) was used to knockdown DEK expression. A lentiviral vector containing the DEK shRNA (pGIPZ-DEK shRNA) (cat. no. RHS4430-99137795) was purchased from Open Biosystems (Thermo-Scientific, Huntsville, Ala.). To prepare DEK-ShRNA lentivirus, $5 \times 10^5$ 293FT cells were first transfected with 10 μg of pGIPZ-DEK shRNA and 5 μg of the packaging vectors (i.e., pCMVΔR8.2 and pHCMV-G) (a gift from Dr. Lairmore, The Ohio State University) (Wei, et al., Journal of Virology, February 2006, p 1242-1249, Vol. 80, No. 3) and grown at 37° C. in 5% $CO_2$. Supernatants of the transfected cells (containing lentivirus particles) were collected at 24 and 48 hours post-transfection. Debris in the supernatants was removed using a 0.45 μm filter.

To obtain DEK knockdown UroTSA cell line, $10^8$ UroTSA cells was transduced with DEK shRNA lentiviral particles, 5 ml of the virus-containing filtrate was spread onto a 10 mm tissue culture dish containing confluent UroTSA cells. Cells were selected for DEK shRNA expression at 48 hours using puromycin (2.5 μg/μl) (Sigma-Aldrich, St. Louis, Mo.).

8. Preparation of DEK Over-Expressing Cell Lines:

DEK gene (NCBI Accession No. NM_003472.3) was cloned into a lentiviral vector (GATEWAY®). To prepare DEK over-expressing cells, $5 \times 10^5$ 293FT cells were first transfected with the DEK-lentiviral vector pLenti6/V5-DEST Gateway® (cat. no. K4960-00, Invitrogen, Carlsbad, Calif.) and a packaging mix (ViraPower™ BSD Packaging Mix, cat. no. K490-00, Invitrogen, Carlsbad, Calif.). Supernatants from the transfected cells were collected at 24 and 48 hours post-transfection and passed through a 0.45 μm filter at 50,000 rpm for 2 hours to remove debris.

5 ml of the virus-containing filtrate was spread onto a 10 mm tissue culture dish containing confluent UroTSA cells. Cells were selected for DEK-V5 expression at 48 hours using blasticidin (10 μg/μl) (Invitrogen, Carlsbad, Calif.).

9. Conductivity Measurements:

Various concentrations (0.1 mM. 0.25 mM, 0.5 mM, 2.5 mM, 5 mM and 10 mM) of potassium chloride were used to calibrate the conductivity meter (Traceable Expanded-Range Conductivity Meter, VWR, model no. 89094-958). Samples (e.g., urine) were prepared by adding 50 μl of sample to 5 ml of de-ionized water. Conductivity was measured by inserting the conductivity probe into the samples and is expressed as μs/cm.

All publications and patents cited in this specification are herein incorporated by reference in their entirety. Although the invention has been described in connection with specific preferred embodiments and certain working examples, it should be understood that the invention as claimed should not be unduly limited to such specific embodiments. Various modifications and variations of the described composition, method, and systems of the invention will be apparent to those skilled in the art without departing from the scope and spirit of the invention.

What is claimed is:

1. A method of detecting bladder cancer in a human, comprising the steps of:
   (a) obtaining a urine sample from a human suspected of bladder cancer;
   (b) forming a precipitate from said urine sample with a chemical compound selected from the group consisting of acetone, trichloroacetic acid, ethanol, methanol/chloroform, and ammonium sulfate;
   (c) re-suspending said precipitate in a polar solvent to form a solution, said solution has a final volume that is 10-50 fold less than that of said urine sample;
   (d) concentrating said solution 2-10 fold by filtration; and
   (e) detecting DEK-2 protein in said concentrated solution using an anti-DEK antibody in a Western blot assay, wherein said detected DEK-2 protein consists of SEQ ID NO: 4, and the presence of said detected DEK-2 protein in said urine sample as compared to a urine sample from a healthy individual is indicative of bladder cancer in said human.

2. The method of claim 1, wherein said chemical compound is acetone.

3. The method of claim 1, wherein said chemical compound and said urine sample has a volume to volume ratio of 2:1.

4. The method of claim 1, wherein said polar solvent is tri-ethanol amine.

5. The method of claim 1, wherein said solution in step (c) has a final volume 20 fold less than that of said urine sample.

6. The method of claim 1, wherein said concentrated solution in step (d) has a final volume 5 fold less than that of said solution.

7. The method of claim 1, wherein said filtration is performed using a filter, said filer has a 3 kD cutoff.

8. The method of claim 1, wherein said anti-DEK antibody is a polyclonal antibody.

9. The method of claim 1, wherein said anti-DEK antibody is labeled with horse radish peroxidase.

10. The method of claim 1, wherein said bladder cancer is transitional cell carcinoma.

* * * * *